United States Patent
Griffiths et al.

(10) Patent No.: US 12,064,201 B2
(45) Date of Patent: *Aug. 20, 2024

(54) SYSTEM AND METHOD FOR MONITORING CONTROL POINTS DURING REACTIVE MOTION

(71) Applicant: INTUITIVE SURGICAL OPERATIONS, INC., Sunnyvale, CA (US)

(72) Inventors: Paul G. Griffiths, Santa Clara, CA (US); Brandon D. Itkowitz, San Jose, CA (US); Goran A. Lynch, Oakland, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/320,331

(22) Filed: May 19, 2023

(65) Prior Publication Data

US 2023/0301735 A1     Sep. 28, 2023

Related U.S. Application Data

(63) Continuation of application No. 17/835,604, filed on Jun. 8, 2022, now Pat. No. 11,737,842, which is a
(Continued)

(51) Int. Cl.
*G06F 17/00* (2019.01)
*A61B 34/20* (2016.01)
(Continued)

(52) U.S. Cl.
CPC .............. *A61B 34/35* (2016.02); *A61B 34/20* (2016.02); *A61B 34/30* (2016.02); *A61B 34/32* (2016.02);
(Continued)

(58) Field of Classification Search
CPC ......... A61B 34/35; A61B 34/20; A61B 34/30; A61B 34/32; A61B 34/37;
(Continued)

(56) References Cited

U.S. PATENT DOCUMENTS

| 4,456,961 A | 6/1984 | Price et al. |
| 4,625,837 A | 12/1986 | Zimmer et al. |

(Continued)

FOREIGN PATENT DOCUMENTS

| CN | 2910169 Y | 6/2007 |
| CN | 101049248 A | 10/2007 |

(Continued)

OTHER PUBLICATIONS

The Robo-Doctor Will See You Now (Year: 2012).*
(Continued)

*Primary Examiner* — Ronnie M Mancho
(74) *Attorney, Agent, or Firm* — Artegis Law Group, LLP

(57) ABSTRACT

Techniques for monitoring control points of a computer-assisted device include one or more articulated arms having one or more control points and a control unit coupled to the one or more articulated arms. Each control point of the one or more control points is located based on a kinematic configuration of the one or more articulated arms. The control unit is configured to determine, during a movement of a table that causes a change in the kinematic configuration of the one or more articulated arms, an actual spatial configuration of the one or more control points; determine, based on a comparison of the actual spatial configuration with an expected spatial configuration of the one or more control points, whether to perform a remedial action; and perform the remedial action in response to a determination to perform the remedial action.

20 Claims, 10 Drawing Sheets

Related U.S. Application Data continuation of application No. 16/862,407, filed on Apr. 29, 2020, now Pat. No. 11,413,103, which is a continuation of application No. 15/522,155, filed as application No. PCT/US2015/057670 on Oct. 27, 2015, now Pat. No. 10,682,190.

(60) Provisional application No. 62/134,252, filed on Mar. 17, 2015, provisional application No. 62/069,245, filed on Oct. 27, 2014.

(51) Int. Cl.
*A61B 34/30* (2016.01)
*A61B 34/32* (2016.01)
*A61B 34/35* (2016.01)
*A61B 34/37* (2016.01)
A61B 17/00 (2006.01)
A61B 18/00 (2006.01)

(52) U.S. Cl.
CPC ........ *A61B 34/37* (2016.02); *A61B 17/00234* (2013.01); *A61B 2018/00898* (2013.01); *A61B 2034/2059* (2016.02)

(58) Field of Classification Search
CPC .... A61B 17/00234; A61B 2018/00898; A61B 2034/2059; A61B 34/70; A61G 13/02
USPC ......................................................... 700/248
See application file for complete search history.

(56) References Cited

U.S. PATENT DOCUMENTS

| | | |
|---|---|---|
| 4,640,663 A | 2/1987 | Niinomi et al. |
| 4,693,665 A | 9/1987 | Friederichs et al. |
| 4,815,006 A | 3/1989 | Andersson et al. |
| 4,894,855 A | 1/1990 | Kresse |
| 4,928,047 A | 5/1990 | Arai et al. |
| 4,945,914 A | 8/1990 | Allen |
| 5,144,213 A | 9/1992 | Sasaki et al. |
| 5,222,499 A | 6/1993 | Allen et al. |
| 5,397,323 A | 3/1995 | Taylor et al. |
| 5,402,801 A | 4/1995 | Taylor |
| 5,657,429 A | 8/1997 | Wang et al. |
| 5,784,542 A | 7/1998 | Ohm et al. |
| 5,790,307 A | 8/1998 | Mick et al. |
| 5,876,325 A | 3/1999 | Mizuno et al. |
| 5,994,864 A | 11/1999 | Inque et al. |
| 6,035,228 A | 3/2000 | Yanof et al. |
| 6,120,433 A | 9/2000 | Mizuno et al. |
| 6,146,200 A | 11/2000 | Ito et al. |
| 6,246,200 B1 | 6/2001 | Blumenkranz et al. |
| 6,424,885 B1 | 7/2002 | Niemeyer et al. |
| 6,471,165 B2 | 10/2002 | Twisselmann |
| 6,471,167 B1 | 10/2002 | Myers et al. |
| 6,560,492 B2 | 5/2003 | Borders |
| 6,788,018 B1 | 9/2004 | Blumenkranz |
| 7,074,179 B2 | 7/2006 | Wang et al. |
| 7,089,612 B2 | 8/2006 | Rocher et al. |
| 7,155,315 B2 | 12/2006 | Niemeyer et al. |
| 7,155,316 B2 | 12/2006 | Sutherland et al. |
| 7,189,246 B2 | 3/2007 | Otsuka et al. |
| 7,720,322 B2 | 5/2010 | Prisco et al. |
| 7,741,802 B2 | 6/2010 | Prisco et al. |
| 7,763,015 B2 | 7/2010 | Cooper et al. |
| 7,837,674 B2 | 11/2010 | Cooper |
| 7,852,030 B2 | 12/2010 | Kamiya |
| 8,004,229 B2 | 8/2011 | Nowlin et al. |
| 8,041,459 B2 | 10/2011 | Sutherland et al. |
| 8,069,714 B2 | 12/2011 | Ortmaier et al. |
| 8,170,717 B2 | 5/2012 | Sutherland et al. |
| 8,226,072 B2 | 7/2012 | Murayama |
| 8,271,130 B2 | 9/2012 | Hourtash et al. |
| 8,396,598 B2 | 3/2013 | Sutherland et al. |
| 8,400,094 B2 | 3/2013 | Schena |
| 8,464,720 B1 | 6/2013 | Pigazzi et al. |
| 8,541,970 B2 | 9/2013 | Nowlin et al. |
| 8,620,473 B2 | 12/2013 | Diolaiti et al. |
| 8,624,537 B2 | 1/2014 | Nowlin et al. |
| 8,641,621 B2 | 2/2014 | Razzaque et al. |
| 8,749,189 B2 | 6/2014 | Nowlin et al. |
| 8,749,190 B2 | 6/2014 | Nowlin et al. |
| 8,786,241 B2 | 7/2014 | Nowlin et al. |
| 8,816,628 B2 | 8/2014 | Nowlin et al. |
| 8,823,308 B2 | 9/2014 | Nowlin et al. |
| 8,852,208 B2 | 10/2014 | Gomez et al. |
| 8,911,499 B2 | 12/2014 | Quaid et al. |
| 8,918,211 B2 | 12/2014 | Diolaiti et al. |
| 9,060,678 B2 | 6/2015 | Larkin et al. |
| 9,078,686 B2 | 7/2015 | Schena |
| 9,084,623 B2 | 7/2015 | Gomez et al. |
| 9,102,058 B2 | 8/2015 | Hofmann et al. |
| 9,107,683 B2 | 8/2015 | Houtash et al. |
| 9,138,129 B2 | 9/2015 | Diolaiti |
| 9,220,567 B2 | 12/2015 | Sutherland et al. |
| 9,295,524 B2 | 3/2016 | Schena et al. |
| 9,296,104 B2 | 3/2016 | Swarup et al. |
| 9,333,042 B2 | 5/2016 | Diolaiti et al. |
| 9,334,911 B2 | 5/2016 | Kameta et al. |
| 9,345,544 B2 | 5/2016 | Hourtash et al. |
| 9,375,284 B2 | 6/2016 | Hourtash |
| 9,387,593 B2 | 7/2016 | Bonin et al. |
| 9,415,510 B2 | 8/2016 | Hourtash et al. |
| 9,468,501 B2 | 10/2016 | Hourtash et al. |
| 9,469,034 B2 | 10/2016 | Diolaiti et al. |
| 9,492,235 B2 | 11/2016 | Hourtash et al. |
| 9,492,927 B2 | 11/2016 | Diolaiti et al. |
| 9,615,728 B2 * | 4/2017 | Charles .............. A61B 17/3211 |
| 9,642,606 B2 * | 5/2017 | Charles ................ G16H 20/40 |
| 9,788,909 B2 | 10/2017 | Larkin et al. |
| 9,918,681 B2 | 3/2018 | Wallace et al. |
| 10,028,793 B2 | 7/2018 | Griffiths et al. |
| 10,034,717 B2 | 7/2018 | Miller et al. |
| 10,039,473 B2 * | 8/2018 | Zhao ..................... A61B 5/065 |
| 10,064,689 B2 | 9/2018 | Swarup et al. |
| 10,226,306 B2 | 3/2019 | Itkowitz et al. |
| 10,231,790 B2 | 3/2019 | Quaid et al. |
| 10,258,414 B2 | 4/2019 | O'Grady et al. |
| 10,258,419 B2 | 4/2019 | Auld et al. |
| 10,272,569 B2 | 4/2019 | Swarup et al. |
| 10,376,324 B2 | 8/2019 | Kerdok et al. |
| 10,405,944 B2 | 9/2019 | Swarup et al. |
| 10,485,617 B2 | 11/2019 | Crawford et al. |
| 10,555,777 B2 | 2/2020 | Griffiths et al. |
| 10,603,135 B2 | 3/2020 | Azizian et al. |
| 10,617,479 B2 | 4/2020 | Itkowitz et al. |
| 10,624,807 B2 | 4/2020 | Itkowitz et al. |
| 10,682,190 B2 | 6/2020 | Griffiths et al. |
| 10,905,500 B2 | 2/2021 | Griffiths et al. |
| 10,993,772 B2 | 5/2021 | Itkowitz et al. |
| 11,130,231 B2 | 9/2021 | Swarup et al. |
| 11,173,005 B2 | 11/2021 | Azizian et al. |
| 11,179,221 B2 | 11/2021 | Swarup et al. |
| 11,413,103 B2 * | 8/2022 | Griffiths ................. A61B 34/30 |
| 11,419,687 B2 | 8/2022 | Itkowitz et al. |
| 11,426,245 B2 | 8/2022 | Quaid |
| 11,576,737 B2 | 2/2023 | Itkowitz et al. |
| 11,672,618 B2 | 6/2023 | Itkowitz et al. |
| 11,684,448 B2 | 6/2023 | Swarup et al. |
| 11,737,842 B2 | 8/2023 | Griffiths et al. |
| 11,759,265 B2 | 9/2023 | Griffiths et al. |
| 11,806,875 B2 | 11/2023 | Swarup et al. |
| 2001/0013764 A1 | 8/2001 | Blumenkranz et al. |
| 2002/0082612 A1 | 6/2002 | Moll et al. |
| 2002/0161446 A1 | 10/2002 | Bryan et al. |
| 2003/0192758 A1 | 10/2003 | Murata et al. |
| 2006/0025668 A1 | 2/2006 | Peterson et al. |
| 2006/0101581 A1 | 5/2006 | Blanchard et al. |
| 2006/0149418 A1 | 7/2006 | Anvari |
| 2007/0096670 A1 | 5/2007 | Hashimoto et al. |
| 2007/0185376 A1 | 8/2007 | Wilson et al. |
| 2007/0270685 A1 | 11/2007 | Kang et al. |
| 2007/0287992 A1 | 12/2007 | Diolaiti et al. |

(56) References Cited

U.S. PATENT DOCUMENTS

| | | |
|---|---|---|
| 2008/0004633 A1 | 1/2008 | Arata et al. |
| 2008/0046122 A1 | 2/2008 | Manzo et al. |
| 2008/0064921 A1 | 3/2008 | Larkin et al. |
| 2008/0125649 A1 | 5/2008 | Meyer et al. |
| 2008/0312529 A1 | 12/2008 | Amiot et al. |
| 2009/0000136 A1 | 1/2009 | Crampton |
| 2009/0024142 A1 | 1/2009 | Ruiz Morales |
| 2009/0088774 A1 | 4/2009 | Swarup et al. |
| 2009/0209976 A1 | 8/2009 | Rosielle |
| 2009/0216372 A1 | 8/2009 | Watanabe et al. |
| 2009/0326324 A1 | 12/2009 | Munoz et al. |
| 2010/0042097 A1 | 2/2010 | Newton et al. |
| 2010/0131102 A1 | 5/2010 | Herzog et al. |
| 2010/0138183 A1 | 6/2010 | Jensen et al. |
| 2010/0168762 A1 | 7/2010 | Osawa et al. |
| 2010/0204713 A1 | 8/2010 | Ruiz Morales |
| 2010/0228249 A1 | 9/2010 | Mohr et al. |
| 2010/0228264 A1 | 9/2010 | Robinson et al. |
| 2010/0286712 A1 | 11/2010 | Won et al. |
| 2010/0292843 A1 | 11/2010 | Kariyazaki et al. |
| 2011/0015521 A1 | 1/2011 | Faul |
| 2011/0071508 A1 | 3/2011 | Duval et al. |
| 2011/0126801 A1 | 6/2011 | Walter |
| 2011/0276179 A1 | 11/2011 | Banks et al. |
| 2011/0282351 A1 | 11/2011 | Cooper et al. |
| 2012/0029694 A1 | 2/2012 | Muller |
| 2012/0101508 A1 | 4/2012 | Wook Choi et al. |
| 2013/0072822 A1 | 3/2013 | Auchinleck et al. |
| 2013/0085510 A1 | 4/2013 | Stefanchik et al. |
| 2013/0096701 A1 | 4/2013 | Suorajaervi et al. |
| 2013/0110129 A1 | 5/2013 | Reid et al. |
| 2013/0123799 A1 | 5/2013 | Smith et al. |
| 2013/0205558 A1 | 8/2013 | Sporer et al. |
| 2013/0283980 A1 | 10/2013 | Petrak et al. |
| 2013/0327902 A1 | 12/2013 | Frick et al. |
| 2013/0338679 A1 | 12/2013 | Rosielle et al. |
| 2014/0005488 A1* | 1/2014 | Charles ............ A61B 90/361 606/1 |
| 2014/0005555 A1* | 1/2014 | Tesar ............... A61B 1/0005 600/476 |
| 2014/0005654 A1 | 1/2014 | Batross et al. |
| 2014/0039517 A1 | 2/2014 | Bowling et al. |
| 2014/0039681 A1 | 2/2014 | Bowling et al. |
| 2014/0052153 A1 | 2/2014 | Griffiths et al. |
| 2014/0052154 A1 | 2/2014 | Griffiths et al. |
| 2014/0055489 A1 | 2/2014 | Itkowitz et al. |
| 2014/0163736 A1 | 6/2014 | Azizian et al. |
| 2014/0222207 A1 | 8/2014 | Bowling et al. |
| 2014/0276887 A1 | 9/2014 | Stein et al. |
| 2014/0305995 A1 | 10/2014 | Shelton, IV et al. |
| 2014/0316252 A1 | 10/2014 | Kwak et al. |
| 2014/0316430 A1 | 10/2014 | Hourtash et al. |
| 2014/0350387 A1 | 11/2014 | Siewerdsen et al. |
| 2014/0358161 A1 | 12/2014 | Hourtash et al. |
| 2015/0032126 A1 | 1/2015 | Nowlin et al. |
| 2015/0051733 A1 | 2/2015 | Nowlin et al. |
| 2015/0117601 A1 | 4/2015 | Keeve et al. |
| 2015/0119637 A1 | 4/2015 | Alvarez et al. |
| 2015/0150639 A1 | 6/2015 | Diolaiti et al. |
| 2015/0224845 A1 | 8/2015 | Anderson et al. |
| 2016/0000512 A1 | 1/2016 | Gombert et al. |
| 2016/0081754 A1 | 3/2016 | Kostrzewski et al. |
| 2016/0098943 A1 | 4/2016 | Valeev et al. |
| 2016/0113728 A1 | 4/2016 | Piron et al. |
| 2016/0156288 A1 | 6/2016 | Sawamura et al. |
| 2016/0242849 A9 | 8/2016 | Crawford et al. |
| 2017/0079731 A1 | 3/2017 | Griffiths et al. |
| 2017/0086932 A1 | 3/2017 | Auld et al. |
| 2017/0143429 A1 | 5/2017 | Richmond et al. |
| 2017/0265949 A1 | 9/2017 | Crawford et al. |
| 2018/0338808 A1 | 11/2018 | Swarup et al. |
| 2018/0344421 A1 | 12/2018 | Cagle et al. |
| 2019/0183593 A1 | 6/2019 | Hourtash et al. |
| 2019/0192233 A1 | 6/2019 | O'Grady et al. |
| 2019/0216550 A1 | 7/2019 | Eyre et al. |
| 2019/0216555 A1 | 7/2019 | DiMaio et al. |
| 2019/0231460 A1 | 8/2019 | DiMaio et al. |
| 2020/0093549 A1 | 3/2020 | Chin et al. |
| 2021/0113277 A1 | 4/2021 | Griffiths et al. |
| 2021/0220084 A1 | 7/2021 | Swarup et al. |
| 2021/0387338 A1 | 12/2021 | Swarup et al. |
| 2022/0296318 A1 | 9/2022 | Itkowitz et al. |
| 2022/0296320 A1 | 9/2022 | Griffiths et al. |
| 2023/0125548 A1 | 4/2023 | Itkowitz et al. |
| 2023/0263584 A1 | 8/2023 | Itkowitz et al. |
| 2023/0372029 A1 | 11/2023 | Griffiths et al. |

FOREIGN PATENT DOCUMENTS

| | | |
|---|---|---|
| CN | 101049697 A | 10/2007 |
| CN | 101064060 A | 10/2007 |
| CN | 101160104 A | 4/2008 |
| CN | 101217913 A | 7/2008 |
| CN | 101222889 A | 7/2008 |
| CN | 201082167 Y | 7/2008 |
| CN | 101332137 A | 12/2008 |
| CN | 101449292 A | 6/2009 |
| CN | 101466342 A | 6/2009 |
| CN | 101472546 A | 7/2009 |
| CN | 101720269 A | 6/2010 |
| CN | 101827735 A | 9/2010 |
| CN | 101959656 A | 1/2011 |
| CN | 102046360 A | 5/2011 |
| CN | 101443163 B | 8/2011 |
| CN | 102389334 A | 3/2012 |
| CN | 102429726 A | 5/2012 |
| CN | 101234033 B | 6/2012 |
| CN | 102715924 A | 10/2012 |
| CN | 102727312 A | 10/2012 |
| CN | 102727358 A | 10/2012 |
| CN | 103027818 A | 4/2013 |
| CN | 103221015 A | 7/2013 |
| CN | 103315818 A | 9/2013 |
| CN | 103637895 A | 3/2014 |
| CN | 103720514 A | 4/2014 |
| CN | 104002296 B | 5/2016 |
| DE | 3119577 A1 | 12/1982 |
| DE | 10249786 A1 | 5/2004 |
| EP | 1915963 A1 | 4/2008 |
| EP | 1974870 A1 | 10/2008 |
| EP | 2047805 A1 | 4/2009 |
| EP | 2332477 A2 | 6/2011 |
| EP | 2332479 A2 | 6/2011 |
| EP | 2332482 A2 | 6/2011 |
| EP | 2581073 A1 | 4/2013 |
| EP | 2735278 A2 | 5/2014 |
| EP | 2023843 B1 | 3/2016 |
| JP | H05138583 A | 6/1993 |
| JP | H06278063 A | 10/1994 |
| JP | H07185817 A | 7/1995 |
| JP | H07328016 A | 12/1995 |
| JP | H09254079 A | 9/1997 |
| JP | H09300264 A | 11/1997 |
| JP | H11226062 A | 8/1999 |
| JP | 2000107200 A | 4/2000 |
| JP | 2000300579 A | 10/2000 |
| JP | 2002307344 A | 10/2002 |
| JP | 2002345831 A | 12/2002 |
| JP | 2003141701 A | 5/2003 |
| JP | 2003299674 A | 10/2003 |
| JP | 2004216022 A | 8/2004 |
| JP | 2004223128 A | 8/2004 |
| JP | 2004358239 A | 12/2004 |
| JP | 2006263894 A | 10/2006 |
| JP | 2008259607 A | 10/2008 |
| JP | 2008538301 A | 10/2008 |
| JP | 2010194101 A | 9/2010 |
| JP | 2011212837 A | 10/2011 |
| JP | 2012005557 A | 1/2012 |
| JP | 2012239709 A | 12/2012 |
| JP | 2013252427 A | 12/2013 |
| JP | 2015502768 A | 1/2015 |
| KR | 20060135063 A | 12/2006 |
| KR | 20100067846 A | 6/2010 |

(56) References Cited

FOREIGN PATENT DOCUMENTS

| | | | |
|---|---|---|---|
| WO | WO-9403113 A1 | 2/1994 |
| WO | WO-2006039092 A2 | 4/2006 |
| WO | WO-2006069288 A2 | 6/2006 |
| WO | WO-2006079108 A1 | 7/2006 |
| WO | WO-2006124390 A2 | 11/2006 |
| WO | WO-2007136768 A2 | 11/2007 |
| WO | WO-2007136770 A2 | 11/2007 |
| WO | WO-2008002830 A2 | 1/2008 |
| WO | WO-2010068005 A2 | 6/2010 |
| WO | WO-2011060042 A1 | 5/2011 |
| WO | WO-2011060139 A2 | 5/2011 |
| WO | WO-2011109041 A1 | 9/2011 |
| WO | WO-2011143016 A1 | 11/2011 |
| WO | WO-2011143338 A1 | 11/2011 |
| WO | WO-2012064528 A1 | 5/2012 |
| WO | WO-2012158458 A2 | 11/2012 |
| WO | WO-2013048957 A1 | 4/2013 |
| WO | WO-2013071057 A1 | 5/2013 |
| WO | WO-2013181503 A1 | 12/2013 |
| WO | WO-2013181507 A1 | 12/2013 |
| WO | WO-2013181516 A1 | 12/2013 |
| WO | WO-2014028703 A1 | 2/2014 |
| WO | WO-2014146095 A1 | 9/2014 |
| WO | WO-2014146107 A1 | 9/2014 |
| WO | WO-2014146113 A1 | 9/2014 |
| WO | WO-2014146119 A1 | 9/2014 |
| WO | WO-2014146120 A1 | 9/2014 |
| WO | WO-2015142798 A1 | 9/2015 |
| WO | WO-2015142930 A1 | 9/2015 |
| WO | WO-2015142943 A1 | 9/2015 |
| WO | WO-2015142947 A1 | 9/2015 |
| WO | WO-2016069648 A1 | 5/2016 |
| WO | WO-2016069655 A1 | 5/2016 |
| WO | WO-2016069659 A1 | 5/2016 |
| WO | WO-2016069660 A1 | 5/2016 |
| WO | WO-2016069661 A1 | 5/2016 |
| WO | WO-2016069663 A1 | 5/2016 |

OTHER PUBLICATIONS

The Robo-Doctor Will See You Now (2012) (Year: 2012).*
Allied Motion, Patient tables, 2023, 2 pages.
Allied Motion, Surgical Robotic Arm Systems and Hand Tools, 2023, 2 pages.
Extended European Search Report for Application No. 15855456.8, mailed on Sep. 25, 2018, 10 pages.
Extended European Search Report for Application No. EP15854136. 7, mailed on Jun. 7, 2018, 11 pages.
Extended European Search Report for Application No. EP15854253, mailed on May 11, 2018, 11 pages.
Extended European Search Report for Application No. EP15854260. 5, mailed on Jun. 7, 2018, 8 pages.
Extended European Search Report for Application No. EP15855051. 7, mailed on May 3, 2018, 10 pages.
Extended European Search Report for Application No. EP15855097, mailed on Apr. 25, 2018, 11 pages.
Extended European Search Report for Application No. EP15855351. 1, mailed on Apr. 30, 2018, 9 pages.
Extended European Search Report for Application No. EP20182993. 4, mailed on Oct. 2, 2020. 13 pages.
Extended European Search Report for Application No. EP22178252, mailed on Sep. 30, 2022, 07 pages.
Extended European Search Report for European Application No. 21181826.5 dated Oct. 26, 2021, 8 pages.
Hesse S., et al., "Lexikon Der Elektrischen Antriebstechnik," Festo Didactic GmbH & Co. KG, Jan. 1, 2004, 202 pages, XP055260002 [retrieved on Mar. 21, 2016], Retrieved from the Internet: url: http://www.boss.festo-cpx.com/pdf/539265_webprint.pdf/url.
International Search Report and Written Opinion for Application No. PCT/US2015/057656, mailed on Feb. 1, 2016, 11 pages.
International Search Report and Written Opinion for Application No. PCT/US2015/057658, mailed on Feb. 1, 2016, 12 pages.
International Search Report and Written Opinion for Application No. PCT/US2015/057664, mailed on Feb. 1, 2016, 8 pages.
International Search Report and Written Opinion for Application No. PCT/US2015/057669, mailed on Feb. 1, 2016, 9 pages.
International Search Report and Written Opinion for Application No. PCT/US2015/057670, mailed on Feb. 1, 2016, 8 pages.
International Search Report and Written Opinion for Application No. PCT/US2015/057671. mailed on Feb. 1, 2016, 6 pages.
International Search Report and Written Opinion for Application No. PCT/US2015/057673, mailed on Feb. 1, 2016, 10 pages.
Laparoscopic Robert Surgery, Current Perspective and Future Directions, 2020, 10 pages.
Partial Supplementary European Search Report for Application No. EP15855456.8, mailed on May 23, 2018, 11 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Ma Y. and Li Y., "Active Disturbance Compensation Based Robust Control for Speed Regulation System of Permanent Magnet Synchronous Motor," Applied Sciences, (Year: 2019), pp. 1-13.
Wang Y., et al., "Disturbance Compensation based Controller for an Indoor Blimp Robot," Robotics and Autonomous Systems, (Year: 2020), pp. 1-15.
Fresenius., "A Robot at the Operating Table," 2019, 06 Pages.
Office Action for Chinese Application No. CN202010672351, mailed Nov. 28, 2023. 29 pages.

* cited by examiner

SYSTEM AND METHOD FOR MONITORING CONTROL POINTS DURING REACTIVE MOTION

RELATED APPLICATIONS

This application is a continuation of U.S. patent application Ser. No. 17/835,604, entitled "System and Method for Monitoring Control Points During Reactive Motion," which was filed on Jun. 8, 2022, which is a continuation of U.S. patent application Ser. No. 16/862,407, entitled "System and Method for Monitoring Control Points During Reactive Motion," which was filed on Apr. 29, 2020, which is a continuation of U.S. patent application Ser. No. 15/522,155, entitled "System and Method for Monitoring Control Points During Reactive Motion," which was filed on Apr. 26, 2017, which is a U.S. National Stage patent application of International Patent Application No. PCT/US2015/057670, entitled "System and Method for Monitoring Control Points During Reactive Motion," which was filed on Oct. 27, 2015, the benefit of which is claimed, and claims priority to U.S. Provisional Patent Application No. 62/134,252 entitled "System and Method for Monitoring Control Points During Reactive Motion," which was filed on Mar. 17, 2015 and U.S. Provisional Patent Application No. 62/069,245 entitled "System and Method for Integrated Operating Table," which was filed Oct. 27, 2014, each of which are hereby incorporated by reference in their entirety.

TECHNICAL FIELD

The present disclosure relates generally to operation of devices with articulated arms and more particularly to monitoring control points during reactive motion.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more articulated arms and/or end effectors. These one or more articulated arms and/or end effectors each include a combination of links and articulated joints that support motion of the articulated arms and/or end effectors. In many cases, the articulated joints are manipulated to obtain a desired position and/or orientation (collectively, a desired pose) of a corresponding instrument located at a distal end of the links and articulated joints of a corresponding articulated arm. Each of the articulated joints proximal to the instrument provides the corresponding articulated arm with at least one degree of freedom that may be used to manipulate the position and/or orientation of the corresponding instrument. In many cases, the corresponding articulated arms may include at least six degrees of freedom that allow for controlling a x, y, and z position of the corresponding instrument as well as a roll, pitch, and yaw orientation of the corresponding instrument. Each articulated arm may further provide a remote center of motion. In some cases, one or more articulated arms and corresponding remote centers of motion or other points on the articulated arms may be allowed to move in order to track the movement of other parts of the electronic device. For example, when an instrument is inserted into a body opening, such as an incision site or body orifice, on a patient during a surgical procedure and a surgical table on which the patient is placed is undergoing motion, it is important for the articulated arm to be able to adjust the position of the instrument to the changes in the positions of the body opening. Depending upon the design and/or implementation of the articulated arm, the body opening on the patient may correspond to the remote center of motion for the articulated arm.

As each of the one or more articulated arms track the underlying movement, the corresponding articulated arm and/or other parts of the electronic device attempt to compensate for the movement in the body opening. When the articulated arms are not able to fully compensate for the movement of the body opening points, this may result in undesirable and/or unsafe consequences. This lack of compliance with the movement of the incision point may result in injury to the patient, damage to the articulated arms, and/or other undesirable outcomes.

Accordingly, it would be desirable to monitor the ability of the articulated arms to compensate for underlying movement in control points, such as body openings.

SUMMARY

Consistent with some embodiments, a computer-assisted medical device includes one or more articulated arms each having a control point and a control unit coupled to the one or more articulated arms. The one or more articulated arms and corresponding control points are configured to track movement of a surgical table. The control unit monitors a spatial configuration of the one or more control points by determining an expected spatial configuration of the one or more control points during the movement of the surgical table, determining an actual spatial configuration of the one or more control points during the movement of the surgical table, and determining a difference between the expected spatial configuration and the actual spatial configuration.

Consistent with some embodiments, a method of monitoring a spatial configuration of one or more control points of a computer-assisted medical device includes determining an expected spatial configuration of the one or more control points during movement of a surgical table, determining an actual spatial configuration of the one or more control points during the movement of the surgical table, and determining a difference between the expected spatial configuration and the actual spatial configuration. The one or more control points correspond to one or more articulated arms and are configured to track the movement of the surgical table.

Consistent with some embodiments, a non-transitory machine-readable medium includes a plurality of machine-readable instructions which when executed by one or more processors associated with a medical device are adapted to cause the one or more processors to perform a method. The method includes determining an expected spatial configuration of one or more control points during movement of a surgical table, determining an actual spatial configuration of the one or more control points in during the movement of the surgical table, and determining a difference between the expected spatial configuration and the actual spatial configuration. The one or more control points correspond to one or more articulated arms and are configured to track the movement of the surgical table.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. The term "including" means including but not limited to, and each of the one or more individual items included should be considered optional unless otherwise stated. Similarly, the term "may" indicates that an item is optional.

Figure 1:
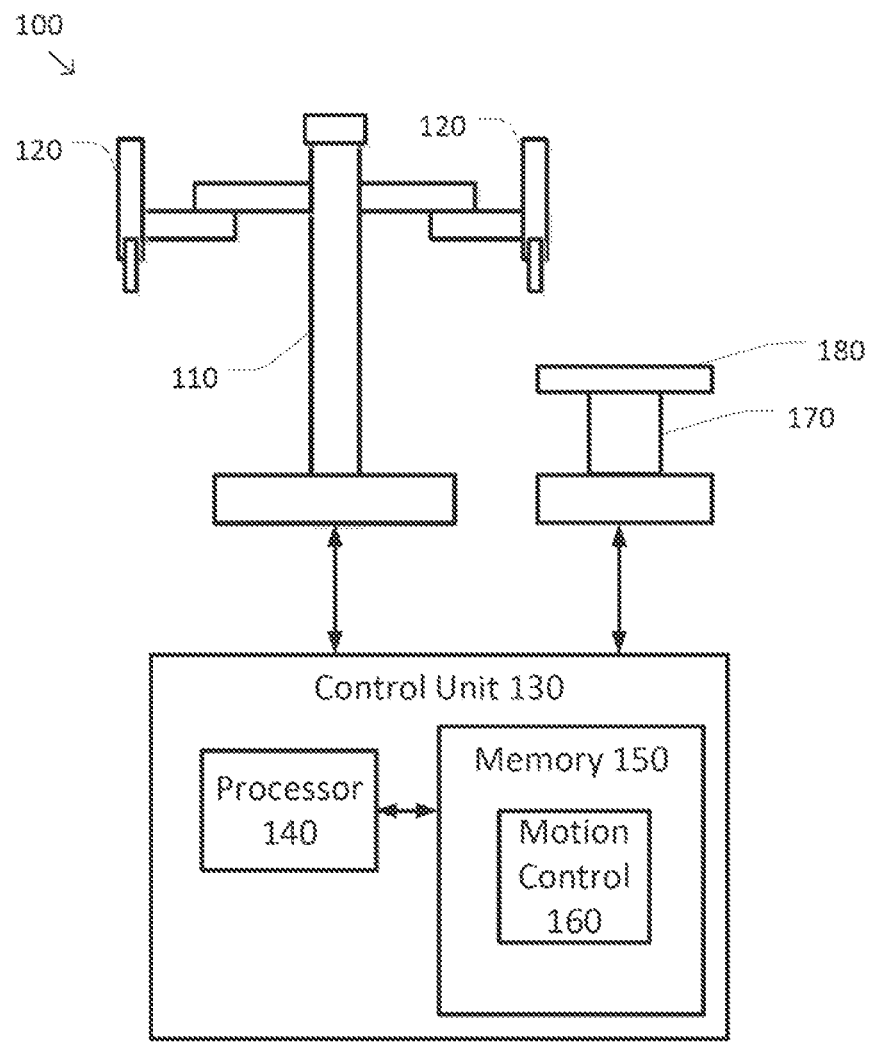
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a device 110 with one or more movable or articulated arms 120. Each of the one or more articulated arms 120 supports one or more end effectors. In some examples, device 110 may be consistent with a computer-assisted surgical device. The one or more articulated arms 120 each provides support for one or more instruments, surgical instruments, imaging devices, and/or the like mounted to a distal end of at least one of the articulated arms 120. Device 110 may further be coupled to an operator workstation (not shown), which may include one or more master controls for operating the device 110, the one or more articulated arms 120, and/or the end effectors. In some embodiments, device 110 and the operator workstation may correspond to a da Vinci® Surgical System commercialized by Intuitive Surgical, Inc. of Sunnyvale, California. In some embodiments, computer-assisted surgical devices with other configurations, fewer or more articulated arms, and/or the like may optionally be used with computer-assisted system 100.

Device 110 is coupled to a control unit 130 via an interface. The interface may include one or more wireless links, cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine. In some embodiments, control unit may be included as part of the operator workstation and/or operated separately from, but in coordination with the operator workstation.

Memory 150 is used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control application 160 that supports autonomous and/or semiautonomous control of device 110. Motion control application 160 may include one or more application programming interfaces (APIs) for receiving position, motion, and/or other sensor information from device 110, exchanging position, motion, and/or collision avoidance information with other control units regarding other devices, such as a surgical table and/or imaging device, and/or planning and/or assisting in the planning of motion for device 110, articulated arms 120, and/or the end effectors of device 110. And although motion control application 160 is depicted as a software application, motion control application 160 may be implemented using hardware, software, and/or a combination of hardware and software.

In some embodiments, computer-assisted system 100 may be found in an operating room and/or an interventional suite. And although computer-assisted system 100 includes only one device 110 with two articulated arms 120, one of ordinary skill would understand that computer-assisted system 100 may include any number of devices with articulated arms and/or end effectors of similar and/or different design from device 110. In some examples, each of the devices may include fewer or more articulated arms and/or end effectors.

Computer-assisted system 100 further includes a surgical table 170. Like the one or more articulated arms 120, surgical table 170 supports articulated movement of a table top 180 relative to a base of surgical table 170. In some examples, the articulated movement of table top 180 may include support for changing a height, a tilt, a slide, a Trendelenburg orientation, and/or the like of table top 180. Although not shown, surgical table 170 may include one or more control inputs, such as a surgical table command unit for controlling the position and/or orientation of table top 180. In some embodiments, surgical table 170 may correspond to one or more of the surgical tables commercialized by Trumpf Medical Systems GmbH of Germany.

Surgical table 170 is also coupled to control unit 130 via a corresponding interface. The interface may include one or more wireless links, cables, connectors, and/or buses and may further include one or more networks with one or more network switching and/or routing devices. In some embodiments, surgical table 170 may be coupled to a different control unit than control unit 130. In some examples, motion control application 160 may include one or more application programming interfaces (APIs) for receiving position, motion, and/or other sensor information associated with surgical table 170 and/or table top 180. In some examples, motion control application 160 may plan and/or assist in the planning of motion for surgical table 170 and/or table top 180. In some examples, motion control application 160 may contribute to motion plans associated with collision avoidance, adapting to and/or avoid range of motion limits in joints and links, movement of articulated arms, instruments, end effectors, surgical table components, and/or the like to compensate for other motion in the articulated arms, instruments, end effectors, surgical table components, and/or the like, adjust a viewing device such as an endoscope to maintain and/or place an area of interest and/or one or more instruments or end effectors within a field of view of the viewing device. In some examples, motion control application 160 may prevent motion of surgical table 170 and/or table top 180, such as by preventing movement of surgical table 170 and/or table top 180 through use of the surgical table command unit. In some examples, motion control application 160 may help register device 110 with surgical table 170 so that a geometric relationship between device 110 and surgical table 170 is known. In some examples, the geometric relationship may include a translation and/or one or more rotations between coordinate frames maintained for device 110 and surgical table 170.

Figure 2:
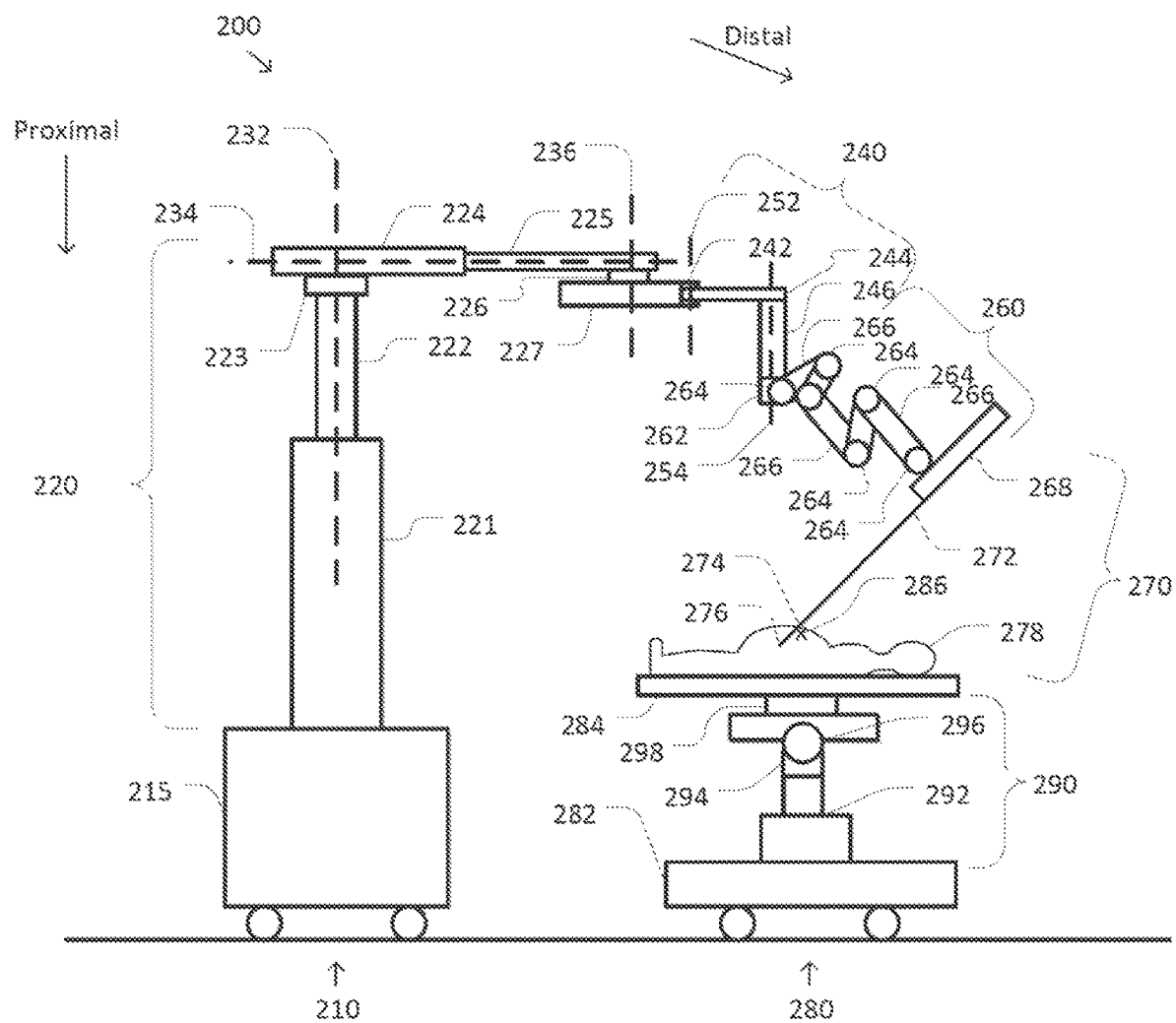
FIG. 2 is a simplified diagram showing a computer-assisted system according to some embodiments.

FIG. 2 is a simplified diagram showing a computer-assisted system 200 according to some embodiments. For example, the computer-assisted system 200 may be consistent with computer-assisted system 100. As shown in FIG. 2, the computer-assisted system 200 includes a computer-assisted device 210 with one or more articulated arms and a surgical table 280. Although not shown in FIG. 2, the computer-assisted device 210 and the surgical table 280 are coupled together using one or more interfaces and one or more control units so that at least kinematic information about the surgical table 280 is known to the motion control application being used to perform motion of the articulated arms of the computer-assisted device 210.

The computer-assisted device 210 includes various links and joints. In the embodiments of FIG. 2, the computer-assisted device is generally divided into three different sets of links and joints. Starting at the proximal end with a mobile cart 215 or patient-side cart 215 is a set-up structure 220. Coupled to a distal end of the set-up structure is a series of links and set-up joints 240 forming an articulated arm. And coupled to a distal end of the set-up joints 240 is a multi-jointed manipulator 260. In some examples, the series of set-up joints 240 and manipulator 260 may correspond to one of the articulated arms 120. And although the computer-assisted device is shown with only one series of set-up joints 240 and a corresponding manipulator 260, one of ordinary skill would understand that the computer-assisted device may include more than one series of set-up joints 240 and corresponding manipulators 260 so that the computer-assisted device is equipped with multiple articulated arms.

As shown, the computer-assisted device 210 is mounted on the mobile cart 215. The mobile cart 215 enables the computer-assisted device 210 to be transported from location to location, such as between operating rooms or within an operating room to better position the computer-assisted device in proximity to the surgical table 280. The set-up structure 220 is mounted on the mobile cart 215. As shown in FIG. 2, the set-up structure 220 includes a two part column including column links 221 and 222. Coupled to the upper or distal end of the column link 222 is a shoulder joint 223. Coupled to the shoulder joint 223 is a two-part boom including boom links 224 and 225. At the distal end of the boom link 225 is a wrist joint 226, and coupled to the wrist joint 226 is an arm mounting platform 227.

The links and joints of the set-up structure 220 include various degrees of freedom for changing the position and orientation (i.e., the pose) of the arm mounting platform 227. For example, the two-part column is used to adjust a height of the arm mounting platform 227 by moving the shoulder joint 223 up and down along an axis 232. The arm mounting platform 227 is additionally rotated about the mobile cart 215, the two-part column, and the axis 232 using the shoulder joint 223. The horizontal position of the arm mounting platform 227 is adjusted along an axis 234 using the two-part boom. And the orientation of the arm mounting platform 227 may also adjusted by rotation about an arm mounting platform orientation axis 236 using the wrist joint 226. Thus, subject to the motion limits of the links and joints in the set-up structure 220, the position of the arm mounting platform 227 may be adjusted vertically above the mobile cart 215 using the two-part column. The positions of the arm mounting platform 227 may also be adjusted radially and angularly about the mobile cart 215 using the two-part boom and the shoulder joint 223, respectively. And the angular orientation of the arm mounting platform 227 may also be changed using the wrist joint 226.

The arm mounting platform 227 is used as a mounting point for one or more articulated arms. The ability to adjust the height, horizontal position, and orientation of the arm mounting platform 227 about the mobile cart 215 provides a flexible set-up structure for positioning and orienting the one or more articulated arms about a work space located near the mobile cart 215 where an operation or procedure is to take place. For example, arm mounting platform 227 may be positioned above a patient so that the various articulated arms and their corresponding manipulators and instruments have sufficient range of motion to perform a surgical procedure on the patient. FIG. 2 shows a single articulated arm coupled to the arm mounting platform 227 using a first set-up joint 242. And although only one articulated arm is shown, one of ordinary skill would understand that multiple articulated arms may be coupled to the arm mounting platform 227 using additional first set-up joints.

The first set-up joint 242 forms the most proximal portion of the set-up joints 240 section of the articulated arm. The set-up joints 240 may further include a series of joints and links. As shown in FIG. 2, the set-up joints 240 include at least links 244 and 246 coupled via one or more joints (not expressly shown). The joints and links of the set-up joints 240 include the ability to rotate the set-up joints 240 relative to the arm mounting platform 227 about an axis 252 using the first set-up joint 242, adjust a radial or horizontal distance between the first set-up joint 242 and the link 246, adjust a height of a manipulator mount 262 at the distal end of link 246 relative to the arm mounting platform 227 along an axis 254, and rotate the manipulator mount 262 about axis 254. In some examples, the set-up joints 240 may further include additional joints, links, and axes permitting additional degrees of freedom for altering a pose of the manipulator mount 262 relative to the arm mounting platform 227.

The manipulator 260 is coupled to the distal end of the set-up joints 240 via the manipulator mount 262. The manipulator 260 includes additional joints 264 and links 266 with an instrument carriage 268 mounted at the distal end of the manipulator 260. An instrument 270 is mounted to the instrument carriage 268. Instrument 270 includes a shaft 272, which is aligned along an insertion axis. The shaft 272 is typically aligned so that it passes through a remote center of motion 274 associated with the manipulator 260. Location of the remote center of motion 274 is typically maintained in a fixed translational relationship relative to the manipulator mount 262 so that operation of the joints 264 in the manipulator 260 result in rotations of the shaft 272 about the remote center of motion 274. Depending upon the embodiment, the fixed translational relationship of the remote center of motion 274 relative to the manipulator mount 262 is maintained using physical constraints in the joints 264 and links 266 of the manipulator 260, using software constraints placed on the motions permitted for the joints 264, and/or a combination of both. Representative embodiments of computer-assisted surgical devices using remote centers of motion maintained using physical constraints in joints and links are described in U.S. patent application Ser. No. 13/906,888 entitled "Redundant Axis and Degree of Freedom for Hardware-Constrained Remote Center Robotic Manipulator," which was filed May 13, 2013, and representative embodiments of computer-assisted surgical devices using remote centers of motion maintained by software constraints are described in U.S. Pat. No. 8,004,229 entitled "Software Center and Highly Configurable Robotic Systems for Surgery and Other Uses," which was filed May 19, 2005, the specifications of which are hereby incorporated by reference in their entirety In some examples, the remote center of motion 274 may correspond to a location of a body opening, such as an incision site or body orifice, in a patient 278 where shaft 272 is inserted into the patient 278. Because the remote center of motion 274 corresponds to the body opening, as the instrument 270 is used, the remote center of motion 274 remains stationary relative to the patient 278 to limit stresses on the anatomy of the patient 278 at the remote center of motion 274. In some examples, the shaft 272 may be optionally passed through a cannula (not shown) located at the body opening. In some examples, instruments having a relatively larger shaft or guide tube outer diameter (e.g., 4-5 mm or more) may be passed through the body opening using a cannula and the cannula may optionally be omitted for instruments having a relatively smaller shaft or guide tube outer diameter (e.g., 2-3 mm or less).

At the distal end of the shaft 272 is an end effector 276. The degrees of freedom in the manipulator 260 due to the joints 264 and the links 266 may permit at least control of the roll, pitch, and yaw of the shaft 272 and/or the end effector 276 relative to the manipulator mount 262. In some examples, the degrees of freedom in the manipulator 260 may further include the ability to advance and/or withdraw the shaft 272 using the instrument carriage 268 so that the end effector 276 may be advanced and/or withdrawn along the insertion axis and relative to the remote center of motion 274. In some examples, the manipulator 260 may be consistent with manipulators for use with the da Vinci® Surgical System commercialized by Intuitive Surgical, Inc. of Sunnyvale, California. In some examples, the instrument 270 may be an imaging device such as an endoscope, a gripper, a surgical instrument such as a cautery or a scalpel, and/or the like. In some examples, the end effector 276 may include additional degrees of freedom, such as roll, pitch, yaw, grip, and/or the like that allow for additional localized manipulation of portions of the end effector 276 relative to the distal end of the shaft 272.

During a surgery or other medical procedure, the patient 278 is typically located on the surgical table 280. The surgical table 280 includes a table base 282 and a table top 284, with the table base 282 being located in proximity to mobile cart 215 so that the instrument 270 and/or end effector 276 may be manipulated by the computer-assisted device 210 while the shaft 272 of instrument 270 is inserted into the patient 278 at the body opening. The surgical table 280 further includes an articulated structure 290 that includes one or more joints or links between the table base 282 and the table top 284 so that the relative location of the table top 284, and thus the patient 278, relative to the table base 282 is controlled. In some examples, the articulated structure 290 may be configured so that the table top 284 is controlled relative to a virtually-defined table motion isocenter 286 that may be located at a point above the table top 284. In some examples, isocenter 286 may be located within the interior of the patient 278. In some examples, isocenter 286 may be collocated with the body wall of the patient at or near one of the body openings, such as a body opening site corresponding to remote center of motion 274.

As shown in FIG. 2, the articulated structure 290 includes a height adjustment joint 292 so that the table top 284 may be raised and/or lowered relative to the table base 282. The articulated structure 290 further includes joints and links to change both the tilt 294 and Trendelenburg 296 orientation of the table top 284 relative to the isocenter 286. The tilt 294 allows the table top 284 to be tilted side-to-side so that either the right or left side of the patient 278 is rotated upward relative to the other side of the patient 278 (i.e., about a longitudinal or head-to-toe (cranial-caudal) axis of the table top 284). The Trendelenburg 296 allows the table top 284 to be rotated so that either the feet of the patient 278 are raised (Trendelenburg) or the head of the patient 278 is raised (reverse Trendelenburg). In some examples, either the tilt 294 and/or the Trendelenburg 296 rotations may be adjusted to generate rotations about isocenter 286. The articulated structure 290 further includes additional links and joints 298 to slide the table top 284 along the longitudinal (cranial-caudal) axis relative to the table base 282 with generally a left and/or right motion as depicted in FIG. 2.

FIGS. 7A-7G are simplified schematic views that illustrate various computer-assisted device system architectures that incorporate the integrated computer-assisted device and movable surgical table features described herein. The various illustrated system components are in accordance with the principles described herein. In these illustrations, the components are simplified for clarity, and various details such as individual links, joints, manipulators, instruments, end effectors, etc. are not shown, but they should be understood to be incorporated in the various illustrated components.

In these architectures, cannulas associated with one or more surgical instruments or clusters of instruments are not shown, and it should be understood that cannulas and other instrument guide devices optionally may be used for instruments or instrument clusters having a relatively larger shaft or guide tube outer diameter (e.g., 4-5 mm or more) and optionally may be omitted for instruments having a relatively smaller shaft or guide tube outer diameter (e.g., 2-3 mm or less).

Also in these architectures, teleoperated manipulators should be understood to include manipulators that during surgery define a remote center of motion by using hardware constraints (e.g., fixed intersecting instrument pitch, yaw, and roll axes) or software constraints (e.g., software-constrained intersecting instrument pitch, yaw, and roll axes). A hybrid of such instrument axes of rotation may be defined (e.g., hardware-constrained roll axis and software-constrained pitch and yaw axes) are also possible. Further, some manipulators may not define and constrain any surgical instrument axes of rotation during a procedure, and some manipulators may define and constrain only one or two instrument axes of rotation during a procedure.

Figure 7A:
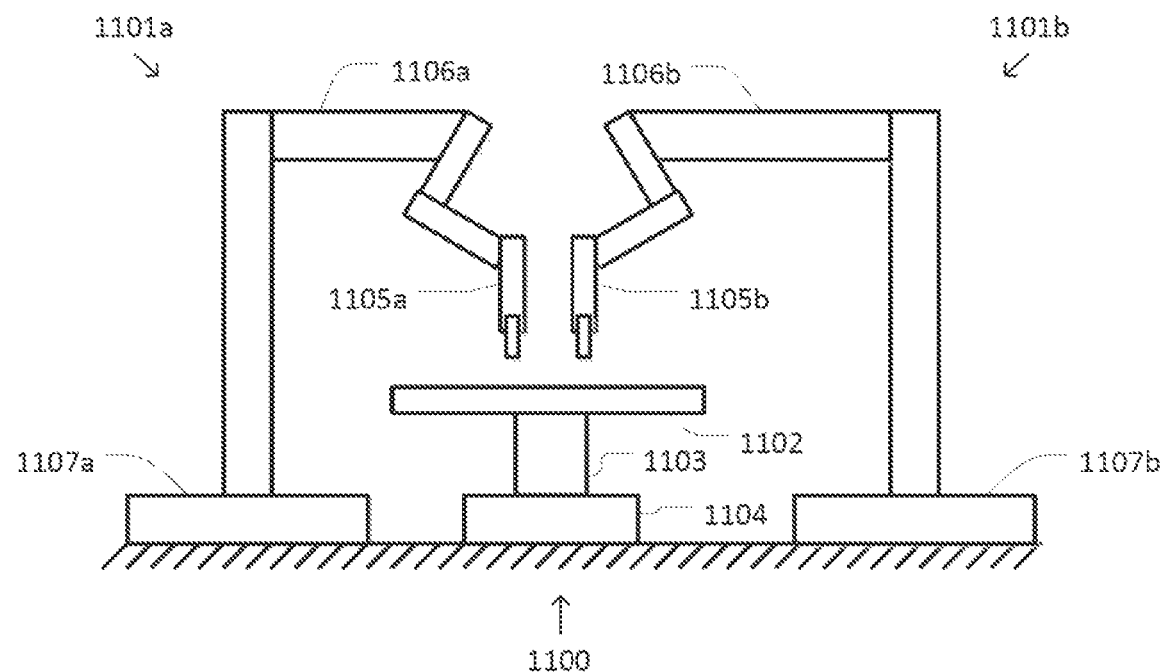
FIGS. 7A-7G are simplified schematic views that illustrate various computer-assisted device system architectures that incorporate the integrated computer-assisted device and movable surgical table features described herein.

FIG. 7A illustrates a movable surgical table 1100 and a single-instrument computer-assisted device 1101a are shown. Surgical table 1100 includes a movable table top 1102 and a table support structure 1103 that extends from a mechanically grounded table base 1104 to support the table top 1102 at a distal end. In some examples, surgical table 1100 may be consistent with surgical table 170 and/or 280. Computer-assisted device 1101a includes a teleoperated manipulator and a single instrument assembly 1105a. Computer-assisted device 1101a also includes a support structure 1106a that is mechanically grounded at a proximal base 1107a and that extends to support manipulator and instrument assembly 1105a at a distal end. Support structure 1106a is configured to allow assembly 1105a to be moved and held in various fixed poses with reference to surgical table 1100. Base 1107a is optionally permanently fixed or movable with reference to surgical table 1100. Surgical table 1100 and computer-assisted device 1101a operate together as described herein.

FIG. 7A further shows an optional second computer-assisted device 1101b, which illustrates that two, three, four, five, or more individual computer-assisted devices may be included, each having a corresponding individual teleoperated manipulator and single-instrument assembly(ies) 1105b supported by a corresponding support structure 1106b. Computer-assisted device 1101b is mechanically grounded, and assemblies 1105b are posed, similarly to computer-assisted device 1101a. Surgical table 1100 and computer-assisted devices 1101a and 1101b together make a multi-instrument surgical system, and they operate together as described herein. In some examples, computer-assisted devices 1101a and/or 1101b may be consistent with computer-assisted devices 110 and/or 210.

Figure 7B:
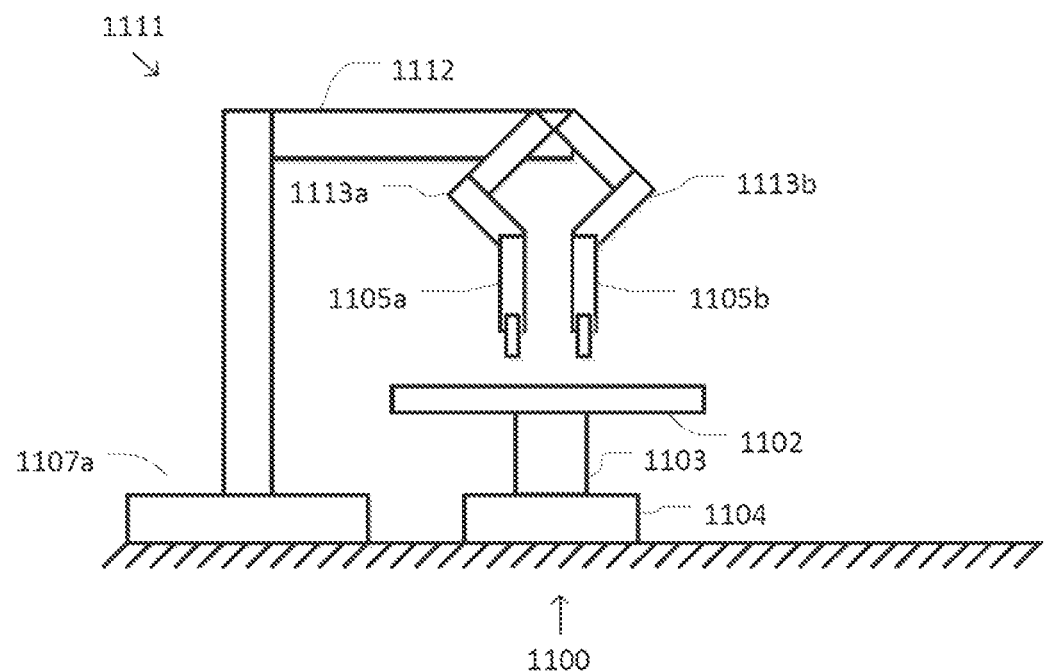

As shown in FIG. 7B, another movable surgical table 1100 and a computer-assisted device 1111 are shown. Computer-assisted device 1111 is a multi-instrument device that includes two, three, four, five, or more individual teleoperated manipulator and single-instrument assemblies as shown by representative manipulator and instrument assemblies 1105a and 1105b. The assemblies 1105a and 1105b of computer-assisted device 1111 are supported by a combined support structure 1112, which allows assemblies 1105a and 1105b to be moved and posed together as a group with reference to surgical table 1100. The assemblies 1105a and 1105b of computer-assisted device 1111 are also each supported by a corresponding individual support structure 1113a and 1113b, respectively, which allows each assembly 1105a and 1105b to be individually moved and posed with reference to surgical table 1100 and to the one or more other assemblies 1105a and 1105b. Examples of such a multi-instrument surgical system architecture are the da Vinci Si® Surgical System and the da Vinci® Xi™ Surgical System, commercialized by Intuitive Surgical, Inc. Surgical table 1100 and a surgical manipulator system comprising an example computer-assisted device 1111 operate together as described herein. In some examples, computer-assisted device 1111 is consistent with computer-assisted devices 110 and/or 210.

Figure 7C:
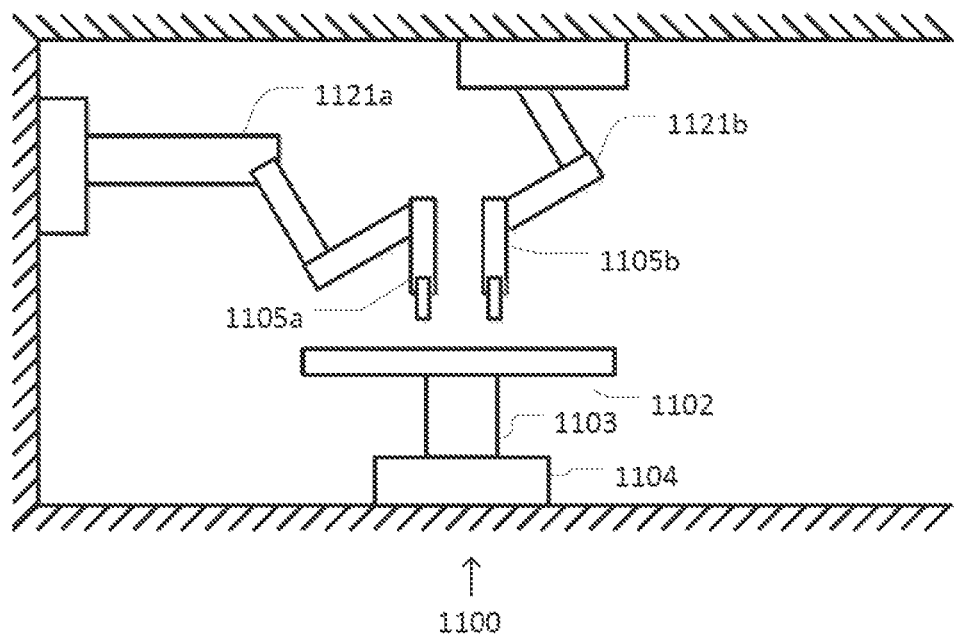

The computer-assisted devices of FIGS. 7A and 7B are each shown mechanically grounded at the floor. But, one or more such computer-assisted devices may optionally be mechanically grounded at a wall or ceiling and be permanently fixed or movable with reference to such a wall or ceiling ground. In some examples, computer-assisted devices may be mounted to the wall or ceiling using a track or grid system that allows the support base of the computer-assisted systems to be moved relative to the surgical table. In some examples, one or more fixed or releasable mounting clamps may be used to mount the respective support bases to the track or grid system. As shown in FIG. 7C, a computer-assisted device 1121a is mechanically grounded at a wall, and a computer-assisted device 1121b is mechanically grounded at a ceiling.

Figure 7D:
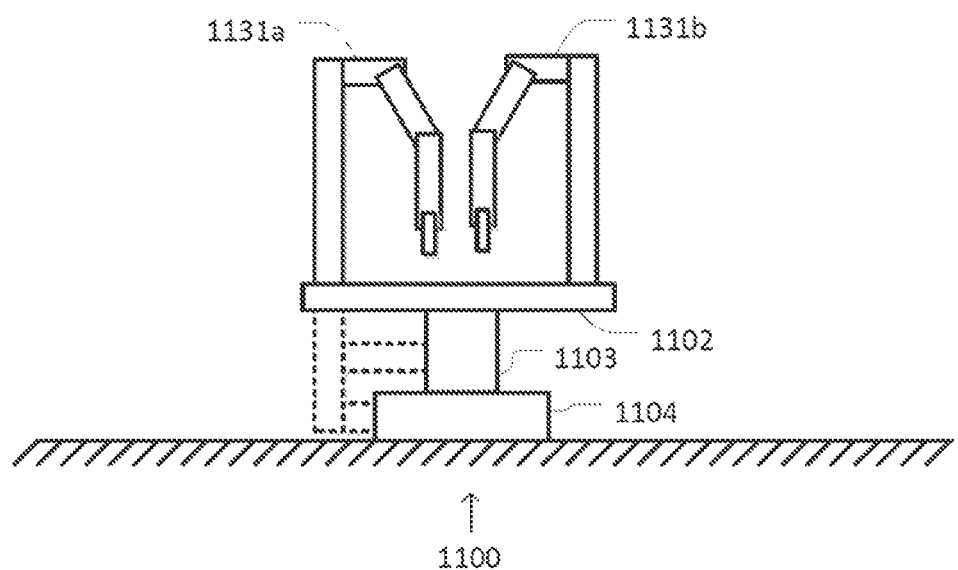

In addition, computer-assisted devices may be indirectly mechanically grounded via the movable surgical table 1100. As shown in FIG. 7D, a computer-assisted device 1131a is coupled to the table top 1102 of surgical table 1100. Computer-assisted device 1131a may optionally be coupled to other portions of surgical table 1100, such as table support structure 1103 or table base 1104, as indicated by the dashed structures shown in FIG. 7D. When table top 1102 moves with reference to table support structure 1103 or table base 1104, the computer-assisted device 1131a likewise moves with reference to table support structure 1103 or table base 1104. When computer-assisted device 1131a is coupled to table support structure 1103 or table base 1104, however, the base of computer-assisted device 1131a remains fixed with reference to ground as table top 1102 moves. As table motion occurs, the body opening where instruments are inserted into the patient may move as well because the patient's body may move and change the body opening locations relative to the table top 1102. Therefore, for embodiments in which computer-assisted device 1131a is coupled to the table top 1102, the table top 1102 functions as a local mechanical ground, and the body openings move with reference to the table top 1102, and so with reference to the computer-assisted device 1131a as well. FIG. 7D also shows that a second computer-assisted device 1131b optionally may be added, configured similarly to computer-assisted device 1131a to create a multi-instrument system. Systems that include one or more computer-assisted device coupled to the surgical table operate as disclosed herein.

In some embodiments, other combinations of computer-assisted devices with the same or hybrid mechanical groundings are possible. For example, a system may include one computer-assisted device mechanically grounded at the floor, and a second computer-assisted device mechanically grounded to the floor via the surgical table. Such hybrid mechanical ground systems operate as disclosed herein.

Figure 7E:
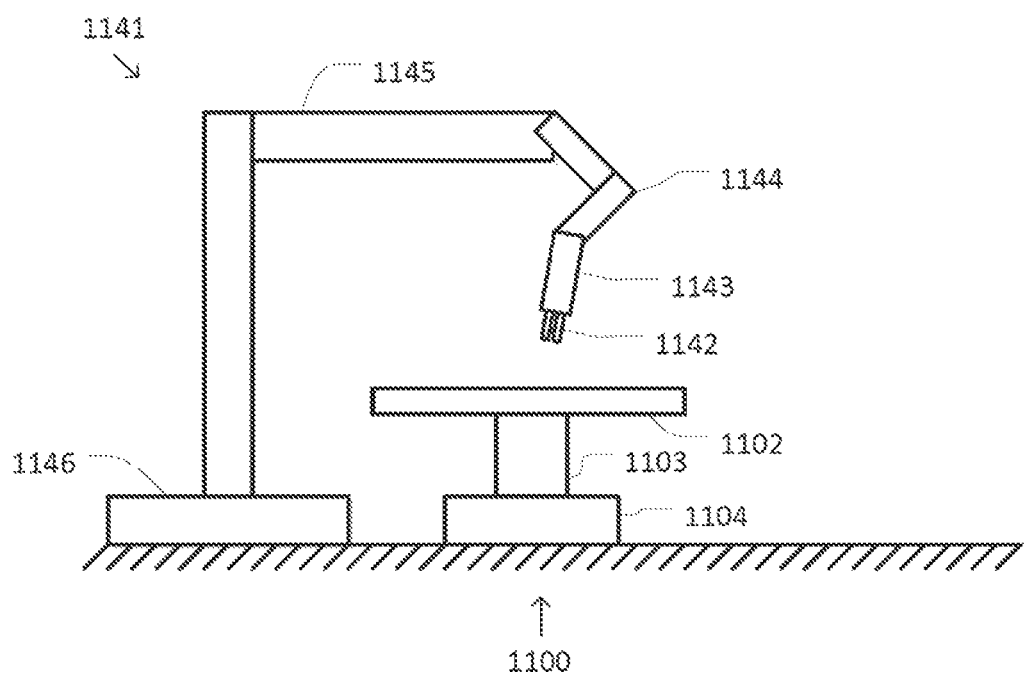

Inventive aspects also include single-body opening systems in which two or more surgical instruments enter the body via a single body opening. Examples of such systems are shown in U.S. Pat. No. 8,852,208 entitled "Surgical System Instrument Mounting," which was filed Aug. 12, 2010, and U.S. Pat. No. 9,060,678 entitled "Minimally Invasive Surgical System," which was filed Jun. 13, 2007, both of which are incorporated by reference. FIG. 7E illustrates a teleoperated multi-instrument computer-assisted device 1141 together with surgical table 1100 as described above. Two or more instruments 1142 are each coupled to a corresponding manipulator 1143, and the cluster of instruments 1142 and instrument manipulators 1143 are moved together by a system manipulator 1144. The system manipulator 1144 is supported by a support assembly 1145 that allows system manipulator 1144 to be moved to and fixed at various poses. Support assembly 1145 is mechanically grounded at a base 1146 consistent with the descriptions above. The two or more instruments 1142 are inserted into the patient at the single body opening. Optionally, the instruments 1142 extend together through a single guide tube, and the guide tube optionally extends through a cannula, as described in the references cited above. Computer-assisted device 1141 and surgical table 1100 operate together as described herein.

Figure 7F:
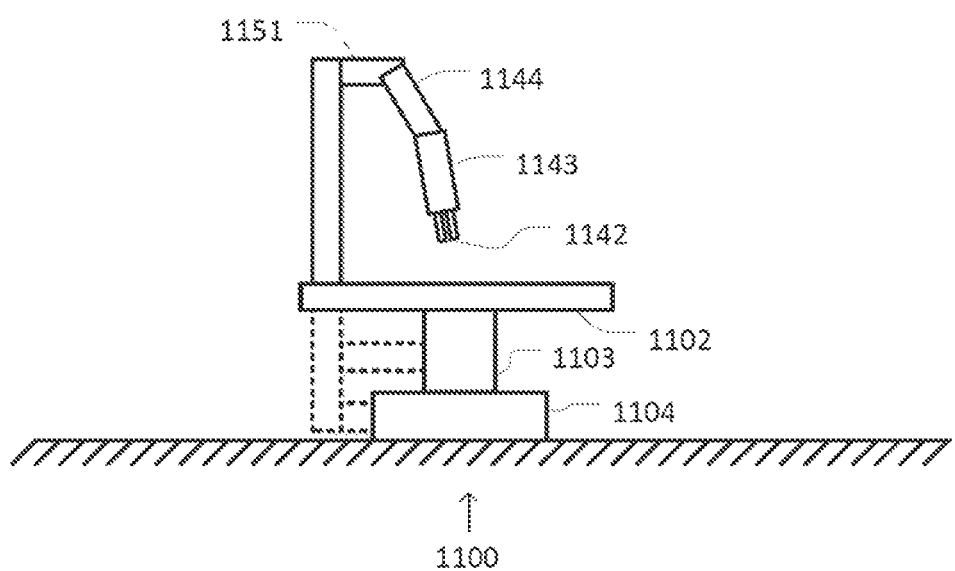

FIG. 7F illustrates another multi-instrument, single-body opening computer-assisted device 1151 mechanically grounded via the surgical table 1100, optionally by being coupled to table top 1102, table support structure 1103, or table base 1104. The descriptions above with reference to FIG. 7D also applies to the mechanical grounding options illustrated in FIG. 7F. Computer-assisted device 1151 and surgical table 1100 work together as described herein.

Figure 7G:
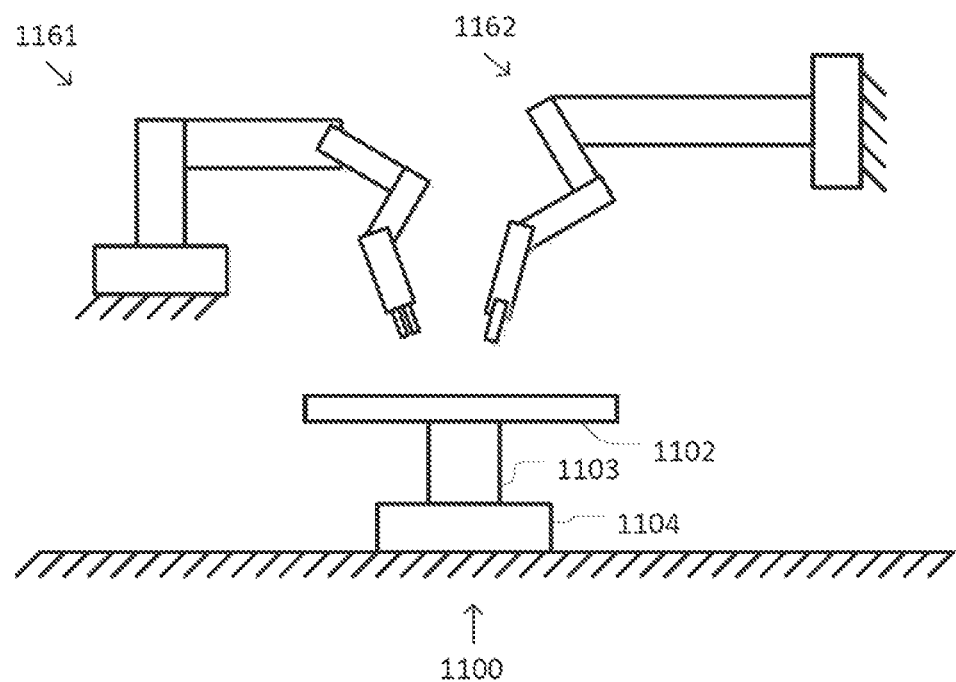

FIG. 7G illustrates that one or more teleoperated multi-instrument, single-body opening computer-assisted devices 1161 and one or more teleoperated single-instrument computer-assisted devices 1162 may be combined to operate with surgical table 1100 as described herein. Each of the computer-assisted devices 1161 and 1162 may be mechanically grounded, directly or via another structure, in various ways as described above.

Figure 3:
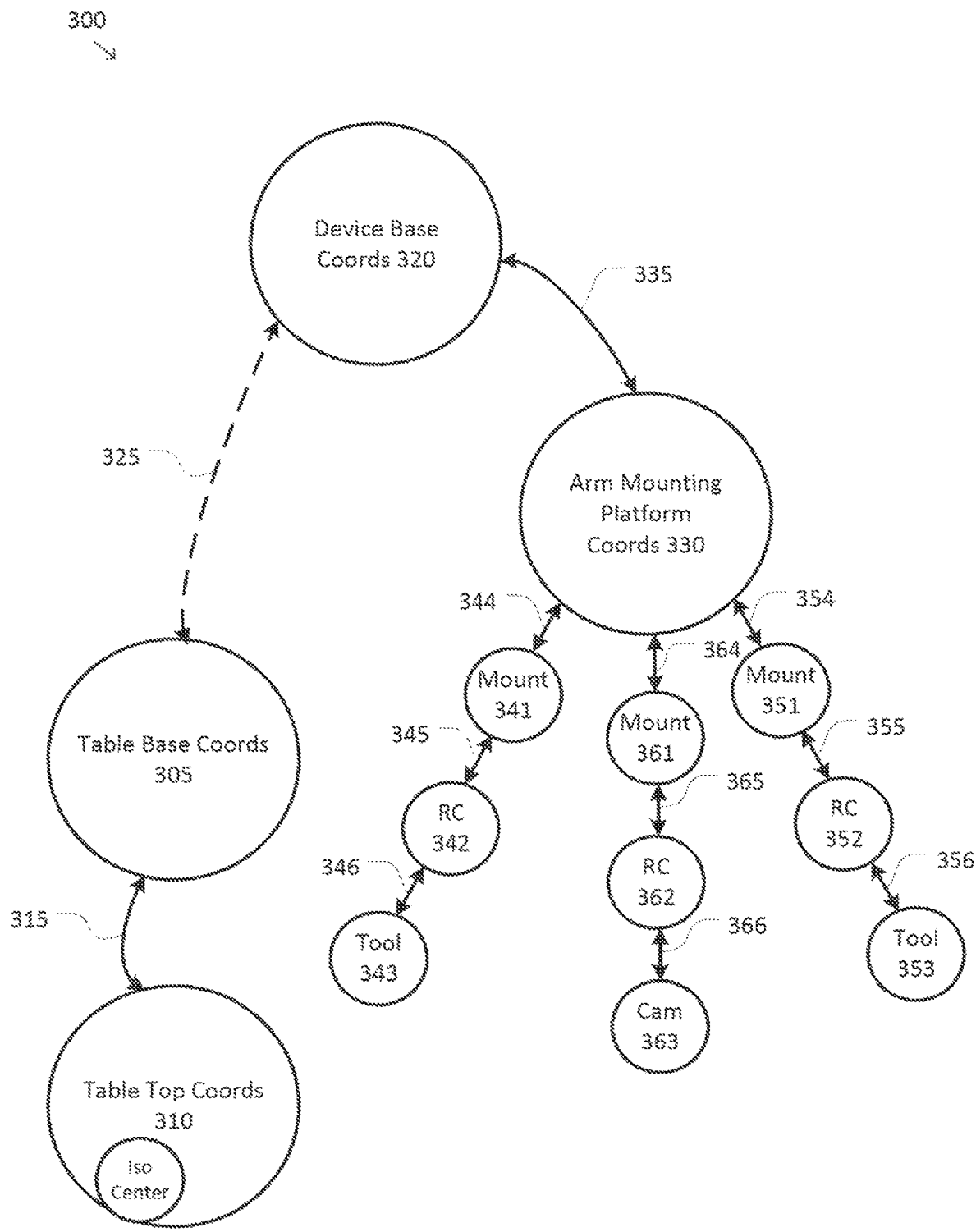
FIG. 3 is a simplified diagram of a kinematic model of a computer-assisted medical system according to some embodiments.

FIG. 3 is a simplified diagram of a kinematic model 300 of a computer-assisted medical system according to some embodiments. As shown in FIG. 3, kinematic model 300 may include kinematic information associated with many sources and/or devices. The kinematic information is based on known kinematic models for the links and joints of a computer-assisted medical device and a surgical table. The kinematic information is further based on information associated with the position and/or orientation of the joints of the computer-assisted medical device and the surgical table. In some examples, the information associated with the position and/or orientation of the joints may be derived from one or more sensors, such as encoders, measuring the linear positions of prismatic joints and the rotational positions of revolute joints.

The kinematic model 300 includes several coordinate frames or coordinate systems and transformations, such as homogeneous transforms, for transforming positions and/or orientation from one of the coordinate frames to another of the coordinate frames. In some examples, the kinematic model 300 may be used to permit the forward and/or reverse mapping of positions and/or orientations in one of the coordinate frames in any other of the coordinate frames by composing the forward and/or reverse/inverse transforms noted by the transform linkages included in FIG. 3. In some examples, when the transforms are modeled as homogenous transforms in matrix form, the composing is accomplished using matrix multiplication. In some embodiments, the kinematic model 300 may be used to model the kinematic relationships of the computer-assisted device 210 and the surgical table 280 of FIG. 2.

The kinematic model 300 includes a table base coordinate frame 305 that is used to model a position and/or orientation of a surgical table, such as surgical table 170 and/or surgical table 280. In some examples, the table base coordinate frame 305 may be used to model other points on the surgical table relative to a reference point and/or orientation associated with the surgical table. In some examples, the reference point and/or orientation may be associated with a table base of the surgical table, such as the table base 282. In some examples, the table base coordinate frame 305 may be suitable for use as a world coordinate frame for the computer-assisted system.

The kinematic model 300 further includes a table top coordinate frame 310 that may be used to model positions and/or orientations in a coordinate frame representative of a table top of the surgical table, such as the table top 284. In some examples, the table top coordinate frame 310 may be centered about a rotational center or isocenter of the table top, such as isocenter 286. In some examples, the z-axis of the table top coordinate frame 310 may be oriented vertically with respect to a floor or surface on which the surgical table is placed and/or orthogonal to the surface of the table top. In some examples, the x- and y-axes of the table top coordinate frame 310 may be oriented to capture the longitudinal (head to toe) and lateral (side-to-side) major axes of the table top. In some examples, a table base to table top coordinate transform 315 is used to map positions and/or orientations between the table top coordinate frame 310 and the table base coordinate frame 305. In some examples, one or more kinematic models of an articulated structure of the surgical table, such as articulated structure 290, along with past and/or current joint sensor readings is used to determine the table base to table top coordinate transform 315. In some examples consistent with the embodiments of FIG. 2, the table base to table top coordinate transform 315 models the composite effect of the height, tilt, Trendelenburg, and/or slide settings associated with the surgical table.

The kinematic model 300 further includes a device base coordinate frame that is used to model a position and/or orientation of a computer-assisted device, such as computer-assisted device 110 and/or computer-assisted device 210. In some examples, the device base coordinate frame 320 may be used to model other points on the computer-assisted device relative to a reference point and/or orientation associated with the computer-assisted device. In some examples, the reference point and/or orientation may be associated with a device base of the computer-assisted device, such as the mobile cart 215. In some examples, the device base coordinate frame 320 may be suitable for use as the world coordinate frame for the computer-assisted system.

In order to track positional and/or orientational relationships between the surgical table and the computer-assisted device, it is often desirable to perform a registration between the surgical table and the computer-assisted device. As shown in FIG. 3, the registration may be used to determine a registration transform 325 between the table top coordinate frame 310 and the device base coordinate from 320. In some embodiments, the registration transform 325 may be a partial or full transform between the table top coordinate frame 310 and the device base coordinate frame 320. The registration transform 325 is determined based on the architectural arrangements between the surgical table and the computer-assisted device.

In the examples of FIGS. 7D and 7F, where the computer-assisted device is mounted to the table top 1102, the registration transform 325 is determined from the table base to table top coordinate transform 315 and knowing where the computer-assisted device is mounted to the table top 112.

In the examples of FIGS. 7A-7C, 7E, and 7F, where the computer-assisted device is placed on the floor or mounted to the wall or ceiling, determination of the registration transform 325 is simplified by placing some restrictions on the device base coordinate frame 320 and the table base coordinate frame 305. In some examples, these restrictions include that both the device base coordinate frame 320 and the table base coordinate frame 305 agree on the same vertical up or z-axis. Under the assumption that the surgical table is located on a level floor, the relative orientations of the walls of the room (e.g., perpendicular to the floor) and the ceiling (e.g., parallel to the floor) are known it is possible for a common vertical up or z axis (or a suitable orientation transform) to be maintained for both the device base coordinate frame 320 and the table base coordinate frame 305 or a suitable orientation transform. In some examples, because of the common z-axis, the registration transform 325 may optionally model just the rotational relationship of the device base to the table base about the z-axis of the table base coordinate frame 305 (e.g., a $\theta_Z$ registration). In some examples, the registration transform 325 may optionally also model a horizontal offset between the table base coordinate frame 305 and the device base coordinate frame 320 (e.g., a XY registration). This is possible because the vertical (z) relationship between the computer-assisted device and the surgical table are known. Thus, changes in a height of the table top in the table base to table top transform 315 are analogous to vertical adjustments in the device base coordinate frame 320 because the vertical axes in the table base coordinate frame 305 and the device base coordinate frame 320 are the same or nearly the same so that changes in height between the table base coordinate frame 305 and the device base coordinate frame 320 are within a reasonable tolerance of each other. In some examples, the tilt and Trendelenburg adjustments in the table base to table top transform 315 may be mapped to the device base coordinate frame 320 by knowing the height of the table top (or its isocenter) and the $\theta_Z$ and/or XY registration. In some examples, the registration transform 325 and the table base to table top transform 315 may be used to model the computer-assisted surgical device as if it were attached to the table top even when this is architecturally not the case.

The kinematic model 300 further includes an arm mounting platform coordinate frame 330 that is used as a suitable model for a shared coordinate frame associated with the most proximal points on the articulated arms of the computer-assisted device. In some embodiments, the arm mounting platform coordinate frame 330 may be associated with and oriented relative to a convenient point on an arm mounting platform, such as the arm mounting platform 227. In some examples, the center point of the arm mounting platform coordinate frame 330 may be located on the arm mounting platform orientation axis 236 with the z-axis of the arm mounting platform coordinate frame 330 being aligned with arm mounting platform orientation axis 236. In some examples, a device base to arm mounting platform coordinate transform 335 is used to map positions and/or orientations between the device base coordinate frame 320 and the arm mounting platform coordinate frame 330. In some examples, one or more kinematic models of the links and joints of the computer-assisted device between the device base and the arm mounting platform, such as the set-up structure 220, along with past and/or current joint sensor readings are used to determine the device base to arm mounting platform coordinate transform 335. In some examples consistent with the embodiments of FIG. 2, the device base to arm mounting platform coordinate transform 335 may model the composite effect of the two-part column, shoulder joint, two-part boom, and wrist joint of the setup structure portion of the computer-assisted device.

The kinematic model 300 further includes a series of coordinate frames and transforms associated with each of the articulated arms of the computer-assisted device. As shown in FIG. 3, the kinematic model 300 includes coordinate frames and transforms for three articulated arms, although one of ordinary skill would understand that different computer-assisted devices may include fewer and/or more articulated arms (e.g., one, two, four, five, or more). Consistent with the configuration of the links and joints of the computer-assisted device 210 of FIG. 2, each of the articulated arms is modeled using a manipulator mount coordinate frame, a remote center of motion coordinate frame, and an instrument or camera coordinate frame, depending on a type of instrument mounted to the distal end of the articulated arm.

In the kinematic model 300, the kinematic relationships of a first one of the articulated arms is captured using a manipulator mount coordinate frame 341, a remote center of motion coordinate frame 342, an instrument coordinate frame 343, an arm mounting platform to manipulator mount transform 344, a manipulator mount to remote center of motion transform 345, and a remote center of motion to instrument transform 346. The manipulator mount coordinate frame 341 represents a suitable model for representing positions and/or orientations associated with a manipulator, such as manipulator 260. The manipulator mount coordinate frame 341 is associated with a manipulator mount, such as the manipulator mount 262 of the corresponding articulated arm. The arm mounting platform to manipulator mount transform 344 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 342 is associated with a remote center of motion of the instrument mounted on the manipulator, such as the corresponding remote center of motion 274 of the corresponding manipulator 260. The manipulator mount to remote center of motion transform 345 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the manipulator mount to remote center of motion transform 345 includes an essentially static translational component that does not change as the manipulator and instrument are operated and a dynamic rotational component that changes as the manipulator and instrument are operated.

The instrument coordinate frame 343 is associated with an end effector located at the distal end of the instrument, such as the corresponding end effector 276. The remote center of motion to instrument transform 346 is then based on one or more kinematic models of the links and joints of the computer-assisted device that move and/or orient the corresponding instrument, end effector, and remote center of motion, along with past and/or current joint sensor readings. In some examples, the remote center of motion to instrument transform 346 accounts for the orientation at which the shaft, such as the corresponding shaft 272, passes through the remote center of motion and the distance to which the shaft is advanced and/or withdrawn relative to the remote center of motion. In some examples, the remote center of motion to instrument transform 346 may be constrained to reflect that the insertion axis of the shaft of the instrument passes through the remote center of motion and accounts for rotations of the shaft and the end effector about the axis defined by the shaft.

In the kinematic model 300, the kinematic relationships of a second one of the articulated arms is captured using a manipulator mount coordinate frame 351, a remote center of motion coordinate frame 352, an instrument coordinate frame 353, an arm mounting platform to manipulator mount transform 354, a manipulator mount to remote center of motion transform 355, and a remote center of motion to instrument transform 356. The manipulator mount coordinate frame 351 represents a suitable model for representing positions and/or orientations associated with a manipulator, such as manipulator 260. The manipulator mount coordinate frame 351 is associated with a manipulator mount, such as the manipulator mount 262 of the corresponding articulated arm. The arm mounting platform to manipulator mount transform 354 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 352 is associated with a remote center of motion of the manipulator mounted on the articulated arm, such as the corresponding remote center of motion 274 of the corresponding manipulator 260. The manipulator mount to remote center of motion transform 355 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the mount to remote center of motion transform 355 includes an essentially static translational component that does not change as the manipulator and instrument are operated and a dynamic rotational component that changes as the manipulator and instrument are operated.

The instrument coordinate frame 353 is associated with an end effector located at the distal end of the instrument, such as the corresponding instrument 270 and/or end effector 276. The remote center of motion to instrument transform 356 is then based on one or more kinematic models of the links and joints of the computer-assisted device that move and/or orient the corresponding instrument, end effector, and remote center of motion, along with past and/or current joint sensor readings. In some examples, the remote center of motion to instrument transform 356 accounts for the orientation at which the shaft, such as the corresponding shaft 272, passes through the remote center of motion and the distance to which the shaft is advanced and/or withdrawn relative to the remote center of motion. In some examples, the remote center of motion to instrument transform 356 may be constrained to reflect that the insertion axis of the shaft of the instrument passes through the remote center of motion and accounts for rotations of the shaft and the end effector about the insertion axis defined by the shaft.

In the kinematic model 300, the kinematic relationships of a third one of the articulated arms is captured using a manipulator mount coordinate frame 361, a remote center of motion coordinate frame 362, a camera coordinate frame 363, an arm mounting platform to manipulator mount transform 364, a manipulator mount to remote center of motion transform 365, and a remote center of motion to camera transform 366. The manipulator mount coordinate frame 361 represents a suitable model for representing positions and/or orientations associated with a manipulator, such as manipulator 260. The manipulator mount coordinate frame 361 is associated with a manipulator mount, such as the manipulator mount 262 of the corresponding articulated arm. The arm mounting platform to manipulator mount transform 364 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 362 is associated with a remote center of motion of the manipulator mounted on the articulated arm, such as the corresponding remote center of motion 274 of the corresponding manipulator 260. The manipulator mount to remote center of motion transform 365 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the mount to remote center of motion transform 365 includes an essentially static translational component that does not change as the manipulator and instrument are operated and a dynamic rotational component that changes as the manipulator and instrument are operated.

The camera coordinate frame 363 is associated with an imaging device, such an endoscope, mounted on the articulated arm. The remote center of motion to camera transform 366 is then based on one or more kinematic models of the links and joints of the computer-assisted device that move and/or orient the imaging device and the corresponding remote center of motion, along with past and/or current joint sensor readings. In some examples, the remote center of motion to camera transform 366 accounts for the orientation at which the shaft, such as the corresponding shaft 272, passes through the remote center of motion and the distance to which the shaft is advanced and/or withdrawn relative to the remote center of motion. In some examples, the remote center of motion to camera transform 366 may be constrained to reflect that the insertion axis of the shaft of the imaging device passes through the remote center of motion and accounts for rotations of the imaging device about the axis defined by the shaft.

As discussed above and further emphasized here, FIG. 3 is merely an example which should not unduly limit the scope of the claims. One of ordinary skill in the art would recognize many variations, alternatives, and modifications. According to some embodiments, the registration between the surgical table and the computer-assisted device may be determined between the table top coordinate frame 310 and the device base coordinate frame 320 using an alternative registration transform. When the alternative registration transform is used, registration transform 325 is determined by composing the alternative registration transform with the inverse/reverse of the table base to table top transform 315. According to some embodiments, the coordinate frames and/or transforms used to model the computer-assisted device may be arranged differently dependent on the particular configuration of the links and joints of the computer-assisted device, its articulated arms, its end effectors, its manipulators, and/or its instruments. According to some embodiments, the coordinate frames and transforms of the kinematic model 300 may be used to model coordinate frames and transforms associated with one or more virtual instruments and/or virtual cameras. In some examples, the virtual instruments and/or cameras may be associated with previously stored and/or latched instrument positions, projections of instruments and/or cameras due to a motion, reference points defined by a surgeon and/or other personnel, and/or the like.

As described previously, as a computer-assisted system, such as computer-assisted systems 100 and/or 200, is being operated it would be desirable to allow continued control of the instrument and/or end effectors while motion of a surgical table, such as surgical tables 170 and/or 280, is allowed. In some examples, this may allow for a less time-consuming procedure as surgical table motion occurs without having to remove instruments from body openings on the patient. In some examples, this allows a surgeon and/or other medical personnel to monitor organ movement while the surgical table motion is occurring to obtain a more optimal surgical table pose. In some examples, this also permits active continuation of a surgical procedure during surgical table motion. Some modes of operation allow motion of the articulated structure in the surgical table (i.e., table movement) while one or more instruments are inserted into body openings on the patient to the patient. Examples of systems permitting active continuation of a surgical procedure during surgical table motion are shown in U.S. Provisional Patent Application No. 62/134,207 entitled "System and Method for Integrated Surgical Table," which was filed Mar. 17, 2015, and concurrently filed PCT Patent Application No. PCT/US2015/057656 entitled "System and Method for Integrated Surgical Table" and published as WO2016/069648 A1, both of which are hereby incorporated by reference in their entirety. During the table movement, it is generally desired to have the remote centers of motion or other control points, corresponding to body openings, body orifices, and/or locations where an instrument is inserted through an incision site on the patient, move with the patient to limit stresses on the anatomy of the patient at the incision points and/or to maintain instrument positioning. In some examples, this may be accomplished using instrument dragging by releasing and/or unlocking one or more joints of the articulated arm and allowing the body wall of the patient at the body opening to drag the control points and the associated instruments as the patient moves. However, an articulated arm and/or end effector may occasionally encounter a disturbance that results in a loss of the ability to freely track the table movement so that the control points do not remain coincident with the body openings. Examples of disturbances that may cause loss of tracking ability include reaching range of motion limits in the joints of the articulated arms, encountering an obstruction such as a tangled cable, loss of cannula retention (i.e., the cannula associated with a control point slipping out from the body wall at the body opening), movement of the patient on the table, a brake release failure, a collision between two arms and/or between an arm and the patient body, and/or the like. Accordingly, in some examples, it may be desired to monitor the configuration of the control points during table movement to ensure that their actual configuration at a given time is consistent with their expected configuration based on the table motion. When a deviation between the actual and expected configurations of the control points is detected, a corresponding remedial action, such as disabling table movement, braking the articulated arms, alerting the user and/or the like, may be taken. Further, according to some embodiments, it may be desirable to detect and/or report offending arms (i.e., the one or more articulated arms was subject to and/or was most impacted by the disturbance that caused the alert to be raised) to facilitate corrective action.

Figure 4:
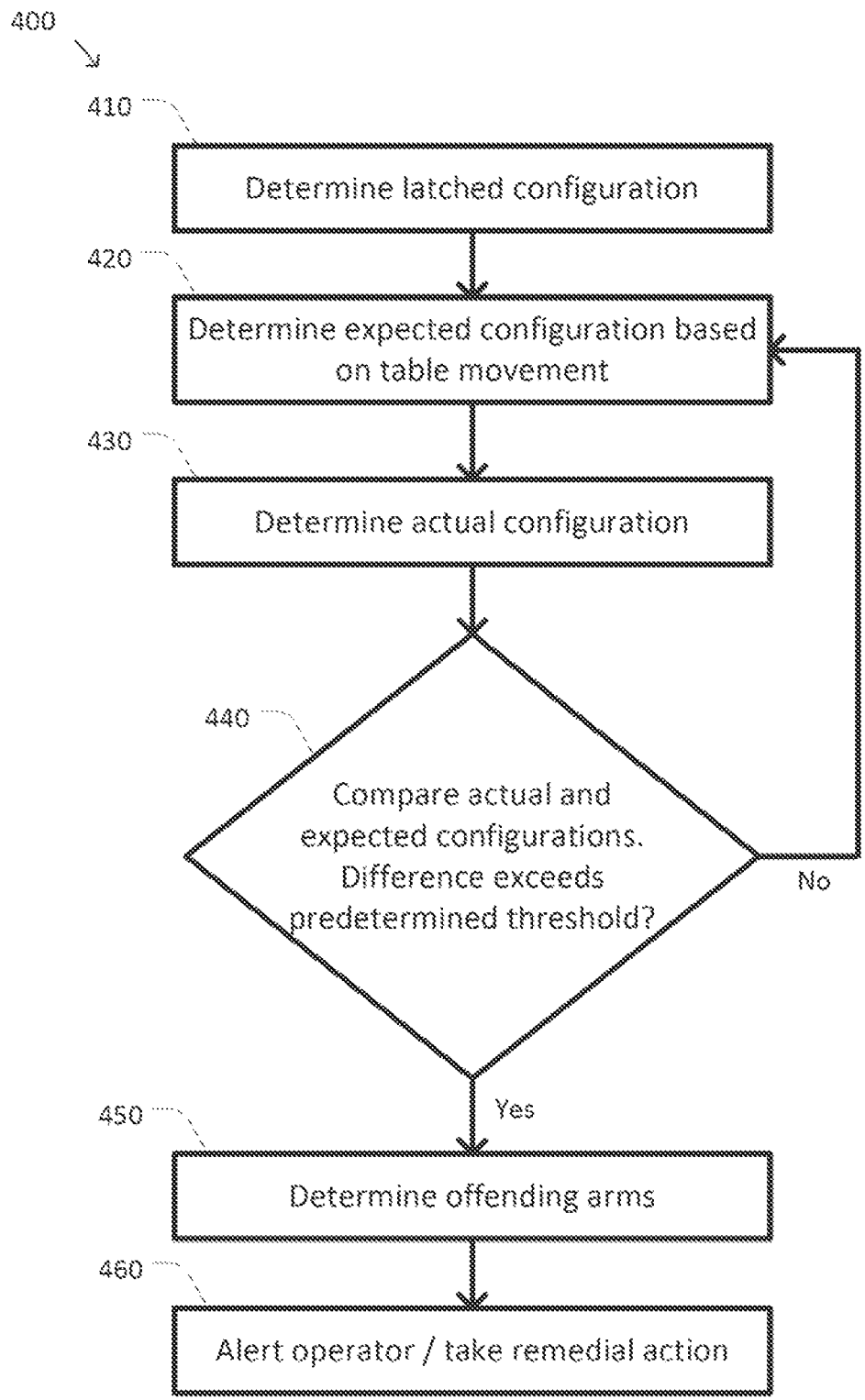
FIG. 4 is a simplified diagram of the method of monitoring one or more control points during table movement according to some embodiments.

FIG. 4 is a simplified diagram of the method 400 of monitoring one or more control points during table movement according to some embodiments. One or more of the processes 410-460 of method 400 may be implemented, at least in part, in the form of executable code stored on non-transient, tangible, machine readable media that when run by one or more processors (e.g., the processor 140 in control unit 130) may cause the one or more processors to perform one or more of the processes 410-460. In some embodiments, method 400 may be used to detect disturbances that prevent control points, such as those located at a body opening, body orifice, or incision site in patient from tracking table movement as expected. In some examples consistent with the embodiments of FIG. 2, the one or more control points may be instances of remote center of motion 274, and table movement may correspond to motion of articulated structure 290 in the surgical table 280. One of ordinary skill would understand that method 400 may be adapted to monitor the movement of remote centers of motion or any other control points that are expected to predictably move as a result of the table movement.

According to some embodiments, method 400 supports one or more useful improvements over methods that do not monitor one or more control points during table movement. In some examples, method 400 may reduce the likelihood of injury to the patient or equipment during table movement by detecting a disturbance that prevents the control points from freely tracking the table movement and allowing a corresponding remedial action to be taken, such as halting table movement and/or alerting an operator of the disturbance. In some examples, method 400 may further facilitate operator intervention by reporting one or more offending arms that were subject to and/or were most impacted by the disturbance. In some examples, method 400 may reduce the likelihood of raising false alarms over other methods by monitoring a selected set of geometric attributes of the control point configuration and/or by setting thresholds that accurately distinguish routine aberrations from unsafe disturbances.

At a process 410, a latched configuration of the control points is determined. The latched configuration specifies one or more attributes of the geometric arrangement of the control points (collectively referred to as the control point constellation) in a reference frame. In some embodiments, the geometric attributes may include the positions of the control points, the orientation of the control point constellation, the point-to-point distances between pairs of control points, the interior angles formed between sets of three control points, the center of curvature of the control point constellation, and/or the like. In some examples, the latched configuration may be determined using sensor readings and/or kinematic models, such as kinematic model 300, to ascertain the position of each control point and/or to derive corresponding geometric attributes of the control point constellation. The selection of the reference frame depends on an operating mode. In some embodiments, the reference frame may be any coordinate frame that is fixed relative to a world coordinate frame. In such examples, consistent with the embodiments of FIGS. 2 and 3, any of the device base coordinate frame 320, arm mounting platform coordinate frame 330, and/or table base coordinate frame 305 may be used as the reference frame. A fixed reference frame may be used in some operating modes for tracking the positions of each control point individually. In some embodiments, the reference frame may be a dynamic coordinate frame where the position of the origin and/or the orientation of the axes of the reference frame depend upon the current position and/or orientation of the control points, table top, and/or other moving components of the system. One example of a dynamic reference frame is a barycentric reference frame, where the origin of the reference frame is an average and/or weighted average position of the control points at a current time and the orientation of the reference frame is fixed relative to a world coordinate frame or a table top coordinate frame. A barycentric reference frame may optionally be used in some operating modes for tracking the movement of the control points relative to one another, in which case common-mode translational motion of the control points (i.e. translational motion that applies to all control points equally) is irrelevant. Once the process 410 is complete, table movement may commence.

At a process 420, an expected configuration of the control points is determined based on the table movement. The expected configuration accounts for predicted changes in the position and/or orientation of the control points relative to the latched configuration determined during process 410 based on table movement. In some embodiments, the expected configuration may specify a set of geometric attributes corresponding to those specified by the latched configuration. In some embodiments, the expected configuration may instead and/or additionally specify one or more differential attributes that are defined relative to the latched configuration, such as a change in position, a change in orientation, and/or the like. In some examples, such as when using instrument dragging, the control points are expected to the move with the table. In such embodiments, for example, when the height of the table changes by a given distance, the vertical position of each of the control points in a fixed reference frame is expected to change by the same distance. Similarly, when the table is rotated by a given angle, such as a tilt, Trendelenburg, and/or reverse Trendelenburg rotation, the orientation of the control point constellation in a barycentric reference frame is expected to rotate by the same angle. According to some embodiments, one or more geometric attributes of the control point constellation is not be expected to change during table movement. For example, the interior angles, point-to-point distances, the center of curvature of the control point constellation, and/or the like is expected to remain constant during table movement.

At a process 430, an actual configuration of the control points during table movement is determined. In some examples, the actual configuration may be determined using position sensors and/or kinematic models to ascertain the position of each control point and/or the corresponding geometric attributes of the control point constellation in the reference frame of the process 410. In some embodiments, the actual configuration specifies a set of geometric attributes that correspond to those specified by the latched configuration of the process 410 and/or the expected configuration determined by process 420.

At a process 440, the actual and expected configurations of the control points are compared to determine if a difference between the configurations exceeds one or more predetermined thresholds. The types and/or values of the predetermined thresholds depend upon the geometric attributes being compared. In some examples, when the geometric attributes include control point positions, the predetermined threshold represents a maximum allowable distance between the actual and expected positions. Similarly, when the geometric attributes include the orientation of the control point constellation, the predetermined threshold represents a maximum allowable angle between the actual and expected orientations. In some examples, when the geometric attributes include a position associated with the control point constellation, such as the centroid position, the predetermined threshold represents a maximum allowable distance between the actual and expected position. In further examples, when the geometric attributes include the center of curvature of the control point constellation, the predetermined threshold represents a restriction that the center of curvature be located below the centroid of the control point constellation. Various other types and/or values of predetermined thresholds may optionally be applied to other geometric attributes in a manner consistent with the underlying characteristics of the attributes being compared.

In general, the values of the predetermined thresholds are selected according to the desire to accurately detect unsafe disturbances to the control point configuration while minimizing false alarms resulting from routine deviations between the actual and expected configurations (e.g., small oscillations in the articulated arms, small lags due to instrument dragging, allowable distortions in the body wall of the patient, and/or the like). In some embodiments, the value of the one or more of the predetermined thresholds is selected based on a clinically acceptable distance that a control point can move relative to the patient's body during table movement. In some embodiments, the clinically acceptable distance is about 12 mm. Thus, in some embodiments, the process 440 may include performing one or more computations to determine a value for a predetermined threshold that is consistent with the clinically acceptable distance being maintained. The computations depend on the characteristics of the geometric attributes being compared. For example, when the geometric attribute is an angle, the computation involves converting the clinically acceptable distance into an equivalent angular value in the reference frame.

Comparing the actual and expected configurations to determine if a difference between the configurations exceeds one or more predetermined thresholds may be achieved in a variety of ways. Thus, the process 440 as described above is merely an example and should not be unduly limiting. According to some examples, rather than converting a clinically acceptable distance into a predetermined threshold consistent with a geometric attribute being compared, the geometric attribute being compared may instead be converted into a distance value consistent with the clinically acceptable distance. According to some examples, rather than comparing the actual and expected configurations directly, a range of allowable values for the geometric attributes of the actual configuration may be determined based on the expected configuration and the predetermined threshold. According to such examples, when the geometric attribute of the actual configuration is not within the range of allowable values, the predetermined threshold is determined to be exceeded.

During the process 440, when it is determined that the one or more predetermined thresholds have not been exceeded, then table movement is allowed to proceed and the method 400 returns to the process 420 to continue monitoring the control point configuration. However, when it is determined that one or more predetermined thresholds have been exceeded, then an alert is raised and the method 400 proceeds to a process 450 described below.

At a process 450, one or more control points and corresponding arms that caused the alert to be raised at the process 440 (referred to as offending arms) are determined. One or more techniques for determining the offending arms may be used. In some embodiments, when a joint reaches a range of motion limit, an articulated arm that corresponds to the range of motion limit event may be identified as an offending arm. In some embodiments, an error value associated with each control point is determined and the corresponding articulated arm with the greatest error value (i.e., the worst offender arm) and/or the one or more corresponding articulated arms with an error value that exceeds a threshold is identified as the one or more offending arms. In some embodiments, when the actual and expected configurations specify actual and expected positions for each control point, the error value includes the distance between the actual and expected positions. In some embodiments, the error value includes the difference between an actual and expected path length, where the path length indicates an amount of distance that each control point has traveled during table motion. To illustrate how the path length difference works, the following example is provided. An expected position travels to the right by 10 units and then to left by 5 units, while an actual position travels to the right by 7 units and to then to the left by 2 units. Both the actual and expected positions end up 5 units to the right of the starting position after the movement, so the distance between the actual and expected positions is 0 units. However, the expected position traveled along a path with a length of 15 units while the actual position traveled a path with a length of 9 units, so the difference between the actual and expected path length is 6 units. Thus, in some embodiments, the path length difference is used to capture certain deviations between the actual and expected positions that are obscured when using the final distance between the actual and expected positions as the error value.

At a process 460, one or more remedial actions are taken based on the alert raised at the process 440 and/or based on the offending arms determined at the process 450. In some embodiments, the remedial actions includes one or more of stopping and/or disabling table movement, alerting an operator to the disturbance, reporting the offending arms to the operator, applying brakes to one or more of the articulated arms, applying compensation to one or more of the articulated arms, logging and/or dispatching an error report, and/or the like. In some embodiments, table movement is stopped as soon as the alert is raised and optionally remains disabled until the operator performs one or more actions, such as manually repositioning the offending arms and/or performing an inspection to identify and correct the disturbances. In some embodiments, the operator may optionally be alerted to the disturbance using an audio, visual, and/or haptic signaling mechanism such as an audio alarm, a flashing light (e.g. an LED), a message on a display screen, a vibration of a surgical table command unit, and/or the like. Similarly, the offending arms may optionally be reported to the operator using any appropriate signaling mechanism, such as the audio, visual, and/or haptic signaling mechanisms mentioned above. In some embodiments, brakes may be fully and/or partially applied to one or more of the articulated arms, including the offending arms and/or all of the articulated arms, to prevent and/or reduce further motion of the control points relative to the table. In some embodiments, an error signal may optionally be sent to one or more joints of the articulated arms to attempt to compensate for the deviation of between the actual and expected configuration by applying a counteracting force to the one or more joints. In some embodiments, an error report, which includes details relevant to the alert being raised such as a timestamp, system identifier, operator identifier, offending arm identifiers, and/or the like, may be logged and/or dispatched to a local and/or remote computer application for informational purposes and/or to allow additional remedial actions to be taken.

As discussed above and further emphasized here, FIG. 4 is merely an example which should not unduly limit the scope of the claims. One of ordinary skill in the art would recognize many variations, alternatives, and modifications. According to some embodiments, method 400 may omit one or more of processes 410-460. For example, some embodiments may omit the process 450 of offending arm detection and alert the operator of disturbances without identifying offending arms. Some embodiments may omit the process 420 of determining an expected configuration (stated differently, the expected configuration may be equivalent to the latched configuration determined at the process 410), particularly when the geometric attributes specified by the latched configuration are not expected to change during table motion. Geometric attributes that are not expected to change during table motion may include point-to-point distances between control points, interior angles formed by sets of three control points, the center of curvature of the control point constellation in a barycentric reference frame, and/or the like. Such embodiments may be used, for example, when no information about the table movement is available and/or when the table movement is performed without convert the table movement into the reference frame of the control point constellation using a registration transform. According to some embodiments, the sequence of the processes 410-460 performed during method 400 may be rearranged and/or one or more of the processes 410-460 may be performed concurrently. In some examples, the process 420 of determining an expected configuration may be performed before, concurrently with, or after the process 430 of determining an actual configuration. In some examples, the process 450 of determining the offending arms may be performed before, concurrently with, or after the process 460 of raising an alert. According to some examples, a plurality of predetermined thresholds may be checked during the process 440 to trigger remedial actions of varying severity at the process 460. For example, a first predetermined threshold may, when exceeded, trigger a warning to the operator at the process 460 but allow continued table movement, and a second predetermined threshold may, when exceeded, disable table movement at the process 460.

Figure 5:
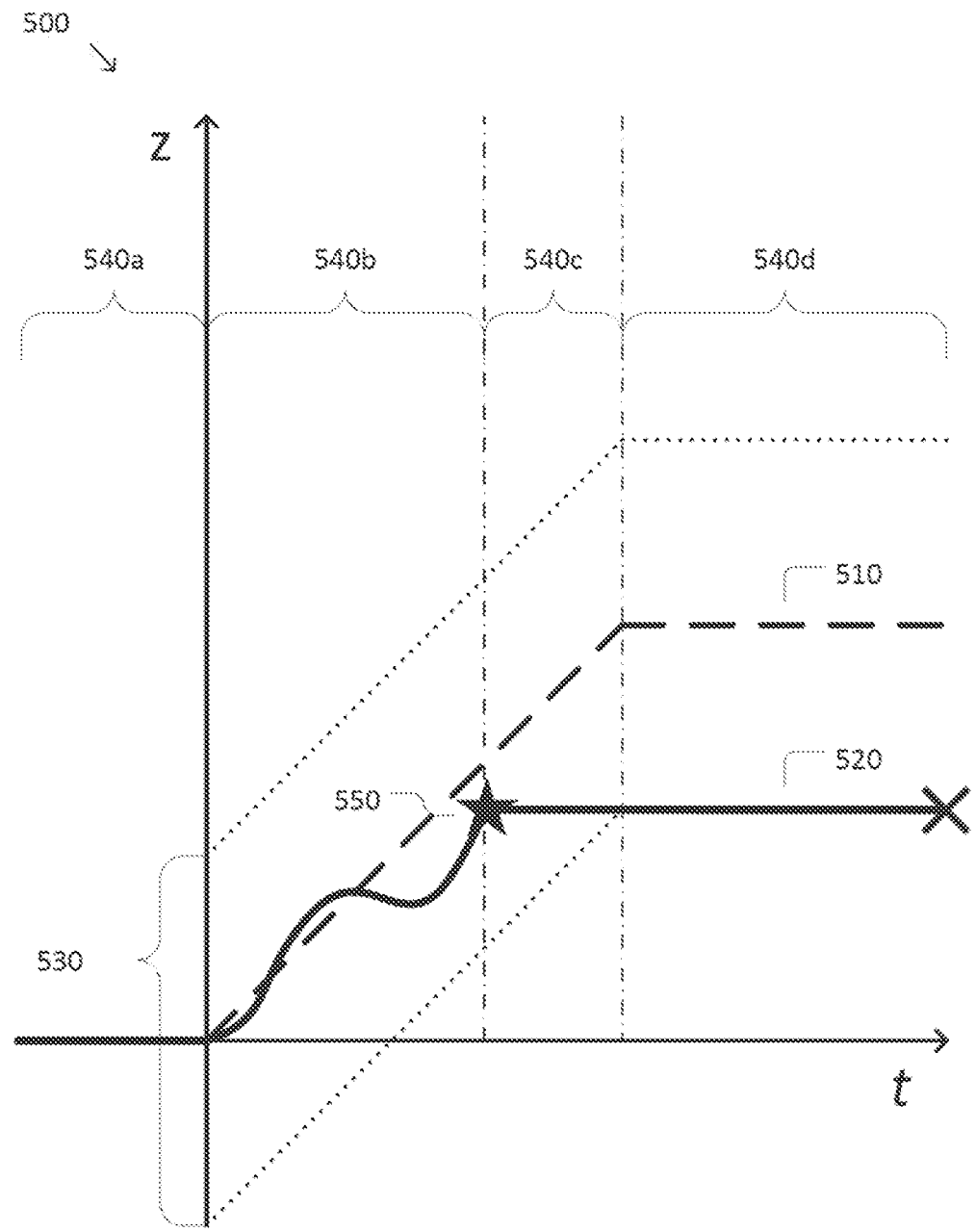
FIG. 5 is a simplified diagram of a control point position during table movement in a height-only mode according to some embodiments.

FIG. 5 is a simplified diagram of a control point position 500 during table movement in a height-only mode according to some embodiments. FIG. 5 depicts traces of vertical position (z axis) versus time (t axis). In some embodiments consistent with the embodiments of FIG. 4, FIG. 5 illustrates an application of the method 400 during table movement in a height-only mode (i.e. where the table movement is restricted to translation in a vertical direction). In some examples consistent with FIGS. 2 and 3, the height-only mode may be enforced when the number of control points being monitored is less than three and/or when the registration between the surgical table and the computer-assisted device has not been performed and the table base to device base transform 325 is not known.

Expected position 510 and actual position 520 are traces that depict an expected position and actual position of a control point over time, respectively. Predetermined threshold 530 is a range of allowable positions corresponding to expected position 510 over time. Phases 540 include a pre-latching phase 540a, a tracking phase 540b, an undetected disturbance phase 540c, and a detected disturbance phase 540d. During pre-latching phase 540a, no table movement is permitted, as the control point monitoring has not yet begun. Between pre-latching phase 540a and tracking phase 540b, a latched position of the control point is determined and height-only table movement is subsequently permitted. In embodiments consistent with FIG. 4, the latched position is determined using the process 410 where the control point configuration specifies the position of the control point in a fixed reference coordinate frame.

During tracking phase 540b, height-only table movement occurs, and the control point freely tracks the table movement. When the table is raised as depicted in FIG. 5, the expected position 510 rises with the table. The actual position 520 generally tracks the expected position 510 during tracking phase 540b, although some small, routine deviations between the actual and expected positions may be observed. In embodiments consistent with FIG. 4, the expected position 510 is determined using the process 420 and the actual position 520 is determined using the process 430. The expected position 510 and actual position 520 may be represented in the reference frame of the latched position and/or differentially represented relative to the latched position. Also during tracking phase 540b, the expected position 510 and actual position 520 are compared to determine whether the actual position 520 is within the allowable range given by the predetermined threshold 530. In embodiments consistent with FIG. 4, the comparison is performed using the process 440 where the value of the predetermined threshold is set to a clinically acceptable distance, such as 12 mm. Although only the vertical component of the allowable range of positions is depicted in FIG. 5 for simplicity, it is to be understood that the comparison may be performed in up to three dimensions, such that a deviation between the expected position 510 and actual position 520 in any direction may be detected. Thus, in some embodiments, the allowable range of positions forms a sphere of allowable positions in three dimensions. As depicted in FIG. 5, during the tracking phase 540b the difference between the expected position 510 and actual position 520 does not exceed the predetermined threshold 530.

Between tracking phase 540b and undetected disturbance phase 540c, a disturbance 550 occurs that prevents the control point from freely tracking the table movement. Disturbance 550 may include any of the disturbances discussed above with respect to FIG. 4, such as encountering an obstacle that blocks the control point from rising beyond a given height as depicted in FIG. 5. Thus, during undetected disturbance phase 540c the actual position 520 no longer closely tracks the expected position 510. However, the distance between the actual position 520 and expected position 510 does not yet exceed the predetermined threshold 530. Therefore, table movement is allowed to continue while the distance between the actual position 520 and expected position 510 approaches the predetermined threshold 530.

Between undetected disturbance phase 540c and detected disturbance phase 540d, the distance between the actual position 520 and expected position reaches the predetermined threshold 530, causing an alert to be raised. In embodiments consistent with FIG. 4, offending arm detection using the process 450 and/or remedial actions using the process 460 may subsequently occur at the beginning of detected disturbance phase 540d. In the embodiment depicted in FIG. 5, table movement is disabled during disturbance detected phase 540d such that the difference between the actual position 520 and expected position 510 does not increase beyond the predetermined threshold 530. Further, when more than one control point is being monitored, the one or more offending arms may be determined using any of the mechanisms discussed previously with respect to the process 450, such as by identifying the control point with the largest difference between actual and expected positions and/or by identifying all of the control points for which the predetermined threshold 530 is exceeded. The operator may optionally be alerted to the detected disturbance and/or the identity of the offending arms by any of the feedback mechanisms discussed with respect to the process 460, such as an audible alarm indicating that a disturbance was detected and/or flashing lights that indicate the offending arms. In some embodiments, table movement may remain disabled until the operator addresses the disturbance, such as by manually repositioning the one or more offending arms.

As discussed above and further emphasized here, FIG. 5 is merely an example which should not unduly limit the scope of the claims. One of ordinary skill in the art would recognize many variations, alternatives, and modifications. According to some embodiments, the z axis of FIG. 5 may represent any geometric attribute of a control point constellation, including a vertical or horizontal position, an orientation, a point-to-point distance, interior angle, and/or the like. Accordingly, procedure 500 may illustrate a method for monitoring any geometric attribute of the control point constellation.

Figure 6:
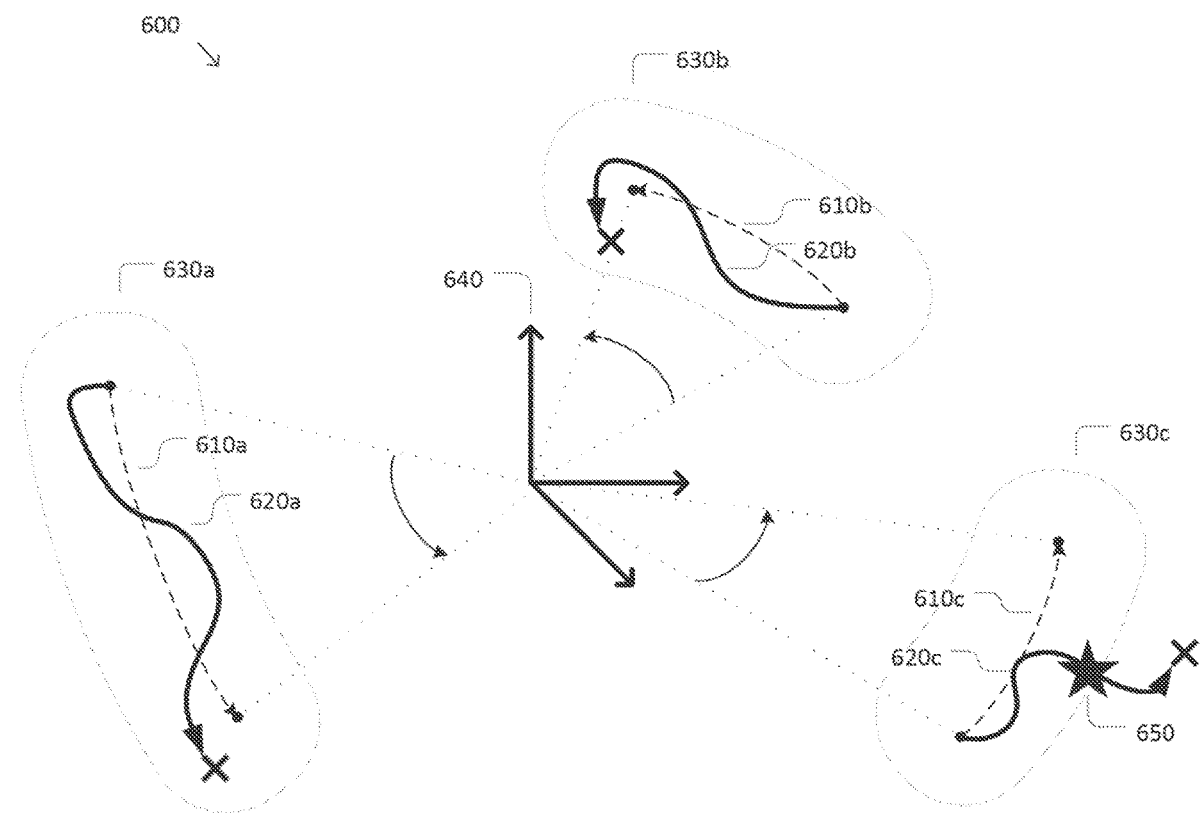
FIG. 6 is a simplified diagram of a control point constellation during rotational table movement according to some embodiments.

FIG. 6 is a simplified diagram of a control point constellation 600 during rotational table movement according to some embodiments. FIG. 6 depicts a three-dimensional arrangement of a control point constellation in a barycentric reference frame with the origin located at the average position of the plurality of control points. In some embodiments consistent with the embodiments of FIG. 4, FIG. 6 illustrates an application of the method 400 to table movement in a mode where rotations such as tilt, Trendelenburg, and/or reverse Trendelenburg rotations are allowed. In some examples consistent with FIGS. 2 and 3, rotational table movement may be allowed when the registration transform 325 is known, such as when the number of control points being monitored is at least three and/or after a registration between the surgical table and the computer-assisted device has been performed.

Expected configuration 610 includes paths 610a-c that represent the expected positions of control points in control point constellation 600 over time, actual configuration 620 includes paths 620a-c that represent actual positions of the control points over time, and predetermined threshold 630 includes ranges of allowable positions 630a-c corresponding to the expected configuration 610 over time. Reference frame 640 represents a barycentric reference frame used to determine the control point positions. Prior to rotating the table and/or prior to determining a latched configuration of the control point constellation, a registration transform is determined. In some embodiments consistent with FIGS. 2 and 3, the registration transform may correspond to registration transform 325 and/or alternate registration transform 325 and may be determined using a $\theta_Z$ registration and/or an XY registration. Accordingly, a rotation of the table relative to table base coordinates 305 by a given angle may be converted into device base coordinates 320 by application of registration transform 325.

At the beginning of table motion, and after $\theta_Z$ and/or XY registration, a latched configuration of the control point constellation is determined. In some embodiments consistent with the embodiments of FIG. 4, the latched configuration is determined using the process 410 in the reference frame 640 before table rotation. The latched configuration specifies the position of each control point and/or one or more geometric attributes of the control point constellation such as the magnitude of the angle formed by the control point constellation relative to the reference frame 640 before table rotation. Once the latched configuration is determined, control point monitoring during table movement begins. In some embodiments consistent with the embodiments of FIG. 4, control point monitoring is performed using the processes 420-440 to determine whether the actual configuration of the control point constellation has deviated from the expected configuration of the control point constellation by more than the predetermined threshold 630. Because reference frame 640 is barycentric, translational movement of the table, such as a height adjustment, slide adjustment, and/or translational movement corresponding to a rotational movement of the table at positions other than an isocenter, does not change the expected configuration 610. Meanwhile, rotational movement of the table changes the orientation of the expected configuration 610, with the direction and magnitude of the change being determined using the detected table movement and the registration transform. It should be noted that although the actual center of the control point constellation may be translating, because the coordinate frames 640 are barycentric it is only the relative positions about the center of the control point constellation that are considered.

Control point constellation 600 illustrates a rotation that results in a change in the orientation of expected configuration relative to the reference frame 640. Like the example shown in FIG. 5, the actual configuration 620 generally tracks the expected configuration 610 within the predetermined threshold 630. For simplicity, the geometric attribute depicted in FIG. 6 is position, but it is to be understood that other geometric attributes, such as the magnitude of the angle formed by the actual configuration 620 relative to reference frame 640, may also be compared with expected configuration 610 and checked against a corresponding threshold value (i.e., a rotation magnitude check).

Control point constellation 600 also illustrates a disturbance 650 that results in control point path 620c diverging from the expected path 610c beyond the allowable range 630c. In some embodiments consistent with the embodiments of FIG. 4, surpassing the threshold results in an alert being raised during the process 440 such that one or more of the processes of offending arm identification 450 and/or remedial action 460 are performed. In some embodiments, the offending arm corresponding to control point path 620c may be determined using any of the mechanisms discussed previously with respect to the process 450, such as by identifying the control point with the largest difference between the actual and expected path lengths. In some embodiments, such as when performing a rotation magnitude check, all of the arms may be identified as offending arms. The operator may be alerted to the detected disturbance and/or the identity of the offending arms by any of the feedback mechanisms discussed with respect to the process 460, such as an audible alarm indicating that a disturbance was detected and/or flashing lights that indicate the offending arm.

As discussed above and further emphasized here, FIG. 6 is merely an example which should not unduly limit the scope of the claims. One of ordinary skill in the art would recognize many variations, alternatives, and modifications. According to some embodiments, control point constellation 600 may include more or less than the three control points depicted. According to some embodiments, the control points may be approximately collinear (i.e. forming a nearly straight line rather than a triangle and/or the like) in which case the sensitivity to rotational movement along one or more axes may decrease. In such embodiments, one or more compensatory actions may be taken when a low sensitivity arrangement is identified, such as disabling rotational table movement, reducing the predetermined thresholds, alerting the operator to the reduced sensitivity and/or increased uncertainty of the monitoring, and/or the like.

Some examples of control units, such as control unit 130 may include non-transient, tangible, machine readable media that include executable code that when run by one or more processors (e.g., processor 140) may cause the one or more processors to perform the processes of method 400. Some common forms of machine readable media that may include the processes of method 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
   one or more articulated arms having one or more control points, wherein each control point of the one or more control points is located based on a kinematic configuration of the one or more articulated arms; and
   a control unit coupled to the one or more articulated arms;
   wherein the control unit is configured to:
      determine, during a movement of a table that causes a change in the kinematic configuration of the one or more articulated arms, an actual spatial configuration of the one or more control points;
      determine, based on a comparison of the actual spatial configuration with an expected spatial configuration of the one or more control points, whether to perform a remedial action; and
      perform the remedial action in response to a determination to perform the remedial action.

2. The computer-assisted device of claim 1, wherein the control unit is further configured to perform the comparison by:
   determining a geometric attribute of the actual spatial configuration;
   determining an expected range for the geometric attribute due to the movement of the table; and determining whether the geometric attribute is within the expected range.

3. The computer-assisted device of claim 2, wherein:
the one or more control points comprises a plurality of control points; and
the geometric attribute is selected from the group consisting of:
a position of a first control point of the plurality of control points,
a distance between two control points of the plurality of control points,
an interior angle formed by three control points of the plurality of control points,
a relative position of the first control point about a center of a control point constellation formed from the plurality of control points,
a position of the center,
an orientation of the control point constellation, and
a center of curvature of the control point constellation.

4. The computer-assisted device of claim 1, wherein the control unit is further configured to perform the comparison by:
determining a difference between a geometric attribute of the actual spatial configuration and a geometric attribute of a previous spatial configuration.

5. The computer-assisted device of claim 1, wherein a first control point of the one or more control points is located based on sensor readings and a kinematic model of a first articulated arm of the one or more articulated arms.

6. The computer-assisted device of claim 1, wherein:
the one or more articulated arms comprises a plurality of articulated arms;
the one or more control points comprises a plurality of control points; and
each control point of the plurality of control points corresponds with an articulated arm of the plurality of articulated arms.

7. The computer-assisted device of claim 1, wherein the control unit is further configured to:
determine a latched spatial configuration of the one or more control points before the movement of the table; and
determine the expected spatial configuration based on the latched spatial configuration.

8. The computer-assisted device of claim 1, wherein the one or more articulated arms and the one or more control points are configured to track the movement of the table using instrument dragging while one or more joints of each of the one or more articulated arms are unlocked.

9. The computer-assisted device of claim 1, wherein a first control point of the one or more control points corresponds to:
a remote center of motion of a first articulated arm of the one or more articulated arms; or
a body opening, a body orifice, an incision site, or a location where an instrument supported by the first articulated arm is inserted into a workspace.

10. The computer-assisted device of claim 1, wherein the remedial action comprises at least one action selected from the group consisting of:
disabling movement of the table,
alerting an operator,
applying compensation to at least one of the one or more articulated arms,
reporting an offending articulated arm, and
logging an error.

11. A method comprising:
determining, by a control unit, a movement of a table separate from a computer-assisted device;
determining, by the control unit during the movement of the table, an actual spatial configuration of one or more control points of one or more articulated arms of the computer-assisted device, the movement of the table causing a change in a kinematic configuration of the one or more articulated arms, wherein each control point of the one or more control points is located based on the kinematic configuration of the one or more articulated arms;
determining, by the control unit based on a comparison of the actual spatial configuration with an expected spatial configuration of the one or more control points, whether to perform a remedial action; and
performing, by the control unit, the remedial action in response to a determination to perform the remedial action.

12. The method of claim 11, further comprising performing, by the control unit, the comparison by:
determining a geometric attribute of the actual spatial configuration;
determining an expected range for the geometric attribute due to the movement of the table; and
determining whether the geometric attribute is within the expected range.

13. The method of claim 11, further comprising performing, by the control unit, the comparison by:
determining a difference between a geometric attribute of the actual spatial configuration and a geometric attribute of a previous spatial configuration.

14. The method of claim 11, further comprising:
determining, by the control unit, a location of each control point of the one or more control points based on sensor readings and a kinematic model of an articulated arm of the one or more articulated arms.

15. The method of claim 11, wherein:
the one or more articulated arms comprises a plurality of articulated arms;
the one or more control points comprises a plurality of control points; and
each control point of the plurality of control points corresponds with an articulated arm of the plurality of articulated arms.

16. The method of claim 11, further comprising:
determining, by the control unit, a latched configuration of the one or more control points before the movement of the table; and
determining, by the control unit, the expected spatial configuration based on the latched configuration.

17. A computer-assisted device comprising:
one or more articulating means having one or more control points, wherein each control point of the one or more control points is located based on a kinematic configuration of the one or more articulating means;
a means for determining, during a movement of a table means that causes a change in the kinematic configuration of the one or more articulating means, an actual spatial configuration of the one or more control points;
a means for comparing the actual spatial configuration with an expected spatial configuration of the one or more control points;
a means for determining, based on the comparing of the actual spatial configuration with the expected spatial configuration, whether to perform a remedial action; and means for performing the remedial action in response to a determination to perform the remedial action.

18. The computer-assisted device of claim 17, wherein the means for comparing comprises:
- a means for determining a geometric attribute of the actual spatial configuration;
- a means for determining an expected range for the geometric attribute due to the movement of the table means; and
- a means for determining whether the geometric attribute is within the expected range.

19. The computer-assisted device of claim 17, wherein the means for comparing comprises:
- a means for determining a difference between a geometric attribute of the actual spatial configuration and a geometric attribute of a previous spatial configuration.

20. The computer-assisted device of claim 17, further comprising:
- a means for determining a latched configuration of the one or more control points before the movement of the table means; and
- a means for determining the expected spatial configuration based on the latched configuration.

* * * * *

UNITED STATES PATENT AND TRADEMARK OFFICE
CERTIFICATE OF CORRECTION

PATENT NO. : 12,064,201 B2
APPLICATION NO. : 18/320331
DATED : August 20, 2024
INVENTOR(S) : Paul G. Griffiths, Brandon D. Itkowitz and Goran A. Lynch Page 1 of 1

It is certified that error appears in the above-identified patent and that said Letters Patent is hereby corrected as shown below:

On the Title Page

(63) Related U.S. Application Data:
Please delete "Continuation of application No. 17/835,604, filed on Jun. 8, 2022, now Pat. No. 11,737,842, which is a continuation of application No. 16/862,407, filed on Apr. 29, 2020, now Pat. No. 11,413,103, which is a continuation of application No. 15/522,155, filed as application No. PCT/US2015/057670 on Oct. 27, 2015, now Pat. No. 10,682,190." and insert --Continuation of application No. 17/835,604, filed on Jun. 8, 2022, now Pat. No. 11,737,842, which is a continuation of application No. 16/862,407, filed on Apr. 29, 2020, now Pat. No. 11,413,103, which is a continuation of application No. 15/522,155, filed on Apr. 26, 2017, now Pat. No. 10,682,190, which is a 371 of application No. PCT/US2015/057670, filed on Oct. 27, 2015.--.

Signed and Sealed this
Fifth Day of November, 2024

Katherine Kelly Vidal
*Director of the United States Patent and Trademark Office*